(12) United States Patent
Cohen et al.

(10) Patent No.: US 6,261,841 B1
(45) Date of Patent: Jul. 17, 2001

(54) COMPOSITIONS, KITS, AND METHODS FOR MODULATING SURVIVAL AND DIFFERENTIATION OF MULTI-POTENTIAL HEMATOPOIETIC PROGENITOR CELLS

(75) Inventors: Isaac Cohen, Wilmette; Phil Lefebvre, Chicago; Jiandie Lin; Daniel Linzer, both of Evanston, all of IL (US)

(73) Assignee: The Board of Trustees of Northwestern University, Evanston, IL (US)

( * ) Notice: Subject to any disclaimer, the term of this patent is extended or adjusted under 35 U.S.C. 154(b) by 0 days.

(21) Appl. No.: 09/602,848

(22) Filed: Jun. 23, 2000

Related U.S. Application Data

(60) Provisional application No. 60/141,060, filed on Jun. 25, 1999, and provisional application No. 60/162,472, filed on Oct. 29, 1999.

(51) Int. Cl.[7] .................. C12N 5/00; C12N 5/02
(52) U.S. Cl. .................. 435/387; 435/377; 435/384; 435/2
(58) Field of Search .................. 435/383–387, 435/377, 2

(56) References Cited

PUBLICATIONS

Lefebvre et al., A Novel Murine Pregnancy Specific Hormone Acts as a Multilineage Survival Factor for Human Bone Marrow Progenitors. (Nov. 15, 1999) Blood vol. 19 No. 10 Suppl. 1 part 1 191a, abstract #837.*
Lin et al. Three Members of the Mouse Prolactin/Growth Hormone Family are Homologous to Proteins Expressed in the Rat (1997) Endochrinology, vol. 138, No. 12, pp. 5541–5549.*
Lin et al. A Novel Megakaryocyte Differentiation Factor from Mouse Placenta (1999) Trends in Cardiovasc. Med. vol. 9, No. 6, pp. 167–171.*
Lin et al., Induction of Megakaryocyte Differentiation by a Novel Pregnancy–specific Hormone (Jul. 23, 1999) J. Biol. Chem., vol. 274, No. 30, pp. 21485–21489.*
Iwatsuki et al., Molecular Cloning and Characterization of a new member of the Rat Placental Prolactin (PRL) Family, PRL–like Protein (PLP–E) (1997) Biology of Reproduction, vol. 56, No. Suppl. 1, p. 220 abstract #552.*
Baatout, 1998, Anticancer Res. 18:1871–1882.
Beaufils et al., 1985, Lancet 1:840–842.
Davison et al., 1989, Baillieres Clin. Endocrinol. Metab. 3:451–472.
Dercksen et al., 1995, Blood 86:3771–3782.
Ellis et al., 1995, Blood Rev. 9:1–6.
Fay et al., 1983, Obst. Gynecol. 61:238–240.
Jackson et al., 1984, Blood 63:768–778.
Kaushansky et al., 1994, Nature 369:568–571.
Konijenberg et al., 1997, Am. J. Obst. Gynecol. 176:461–469.
Lin et al., 1997, Endocrinology 138:5535–5540.
Luens et al., 1998, Blood 91:1206–1215.
Miltenyi et al., 1990, Cytometry 11:231–238.
Muller et al., 1998, Biochim, Biophys. Acta 1396:251–258.
Muller et al., 1998, J. Histochem. Cytochem. 46:737–743.
Nakashima et al., 1998, Semin. Hematol. 35:210–221.
Nyui et al., 1998, Biochem. Biophys. Res. Commun. 245:928–932.
Shavit et al., 1998, Genes Dev. 12:2164–2174.
Steyn et al., 1997, Lancet 350:1267–1271.

* cited by examiner

*Primary Examiner*—Jon P. Weber
*Assistant Examiner*—Harry J Guttman
(74) *Attorney, Agent, or Firm*—Morgan, Lewis & Bockius, L.L.P.

(57) ABSTRACT

The invention includes compositions, kits, and methods for modulating survival and differentiation of mammalian multi-potential hematopoietic progenitor cells using a placental glycoprotein hormone of the murine prolactin family, namely either murine prolactin-like protein E or murine prolactin-like protein F. The compositions, kits, and methods described herein can be used, for example, for in vitro or ex vivo expansion of hematopoietic precursor cells or to treat a disorder associated with aberrant hematopoiesis (e.g., pre-eclampsia and thrombocytopenia).

20 Claims, 13 Drawing Sheets

FIG. 3A
FIG. 3B
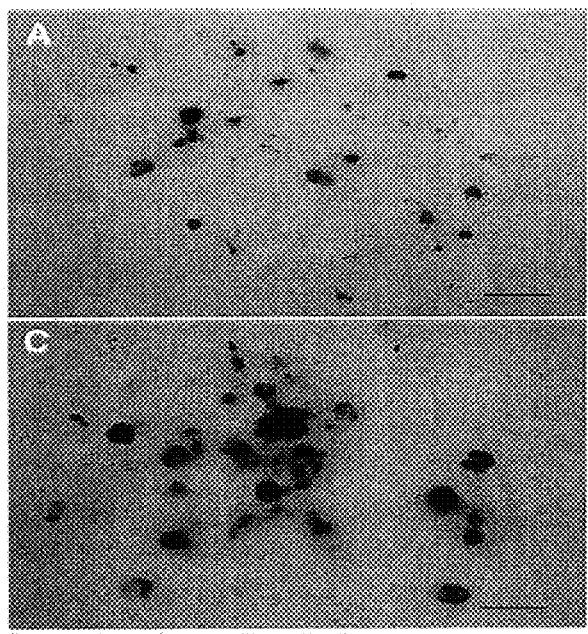
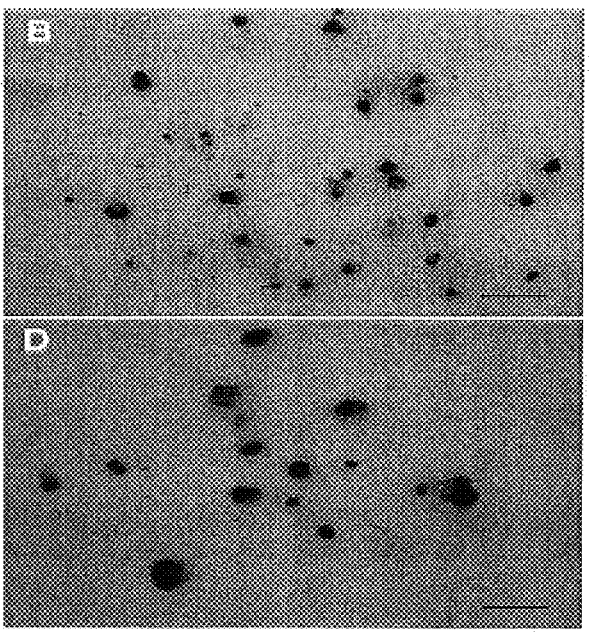
FIG. 3C
FIG. 3D

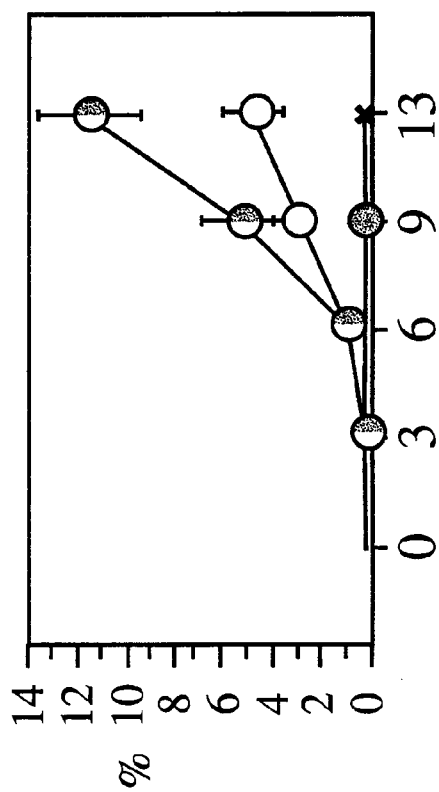
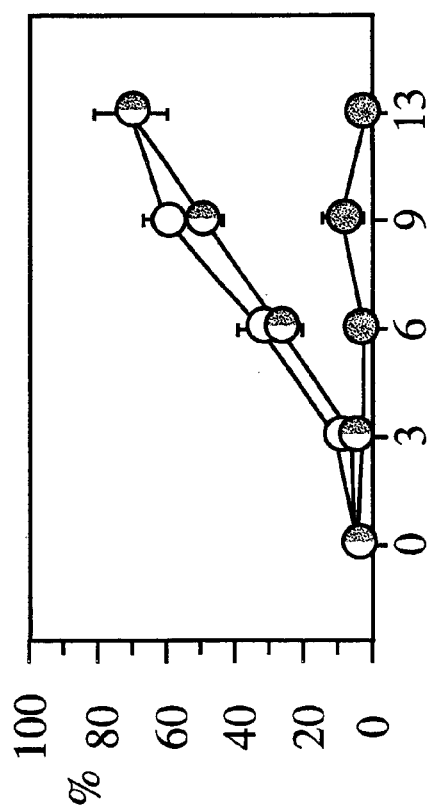
Fig. 8B
Fig. 8A

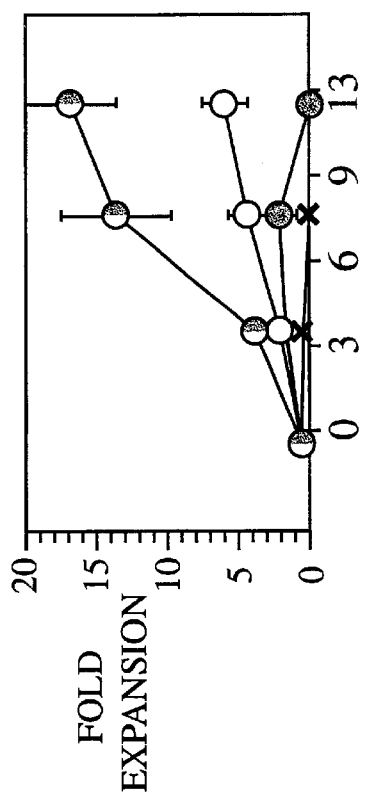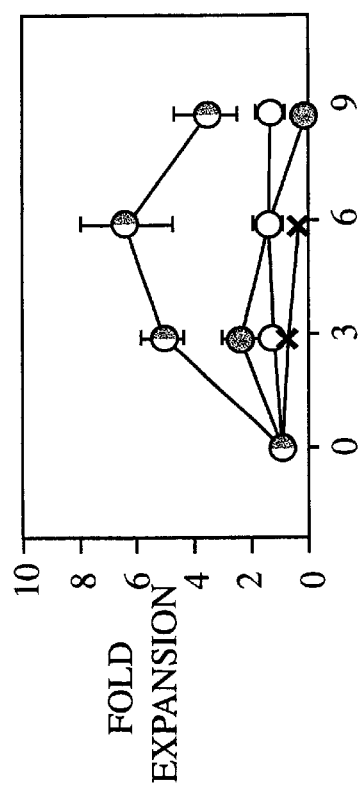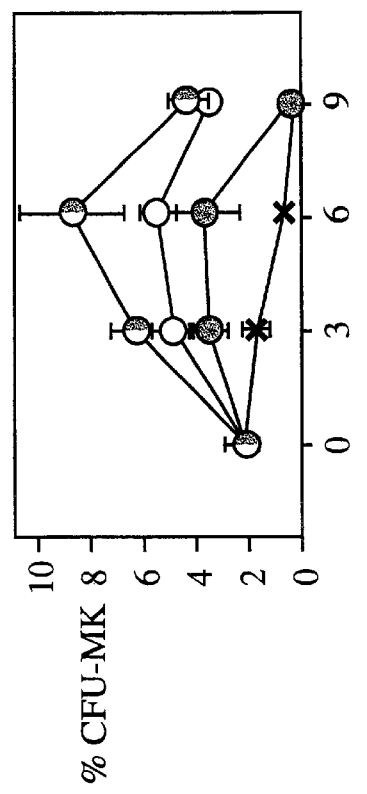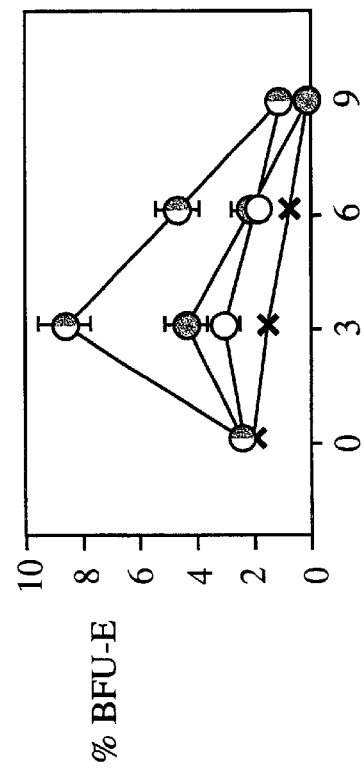
Fig. 9A
Fig. 9B
Fig. 9C
Fig. 9D

Fig. 11A

LPLSSNDTDDDPLSIKGLLDHAMILSKNITDLNMELRRIFTISEMSAKLIDKFLSSSSSDSYDQFMLEFLGQQELLTK
NLTYCHKYSIKVPEDIEEAQNVISLEDFPILILSRMQAWNETLKNRINLSEGTPGIDDDILPIYKNIETKIAELLEDSK
SILSQAYGATENVADYTLWSGLEDLQSSDEETRFLALCKLSYCLHVDIHTANFYLQFLRCVALVNSDSCLSSKTGNDS

Fig. 11B

```
  1  ccacgcgtcc gcaagtgtgc aaggacacct cagagatgcc gctgtctttc actcaaccat
 61  gctcctggc acttctgctg ctggtggtgt caaacctcct tttatgggag aatgtggcct
121  gtctacctt aagcagcaat gatactgatg atccatccact atccatcaag ggactgttgg
181  atcatgccat gatactttct aagaatatca ctgacctcaa catggagttg cgcaggatat
241  ttaccatcag tgagatgtca gctaaactta ttgataaatt tctaagttca tcatcatcat
301  cagactccta tgatcaattt atgcttgaat ttcttgggca gcaggagtta ctgactaaga
361  acctcacta ctgccacaaa tactccatca agttcccga agacatagaa gaagcccaaa
421  atgtcatctc tcttgaagac tttccaatct tgatactcag tagaatgcag gcttggaatg
481  aaactctgaa aaaccgaatc aacctatctg aaggtacacc aggaatagac gatgatatcc
541  tcccctatata taaaaatatt gagacaaaaa ttgcagaact tcttgaggac agcaagagta
601  tactcagcca ggcttatgga gcaacagaaa atgtggctga ttacaccctc tggtctggtc
661  ttgaagacct tcaatcatct gatgaagaaa ctcgatttt ggctcttttgt aaattatcct
721  attgttgca tgttgatatc cacacagcta acttttatct ccagttcttg aggtgtgtgg
781  ctcttgttaa tagtgacagc tgcttatctt ccaaaactgg aaatgattca tgatgctgta
841  ttatttaaa atagtctgat tttatgcatt tcaaagatga gcatgagtaa aatgggcatc
901  ttttaaaaga aaataaaca ttgtgtgttt aac
```

VPLSSNETDGYPLSINGLFHNAMRLTWNIKNLNMELRKTYTVNQVSEKLYENYMLDFEIEDMEYLVKALTCCHNYSIKTP
ENLDEAQQIPFNEFPKLILSRMWAWNETSKVLLTTLRSIPGMHDDVISLAKNIETKLAELFEYTQSILNSIYGTTTTGN
VEYTVFSGLEDLKSSDEEFSLFDLCKFSYCLRVDIHMVELYLKLLECVVYVSSDVCLSKNIRDAS

Fig. 12A

```
  1 ggcagacagg ctgtgccaga actcttcaga gatgtcattt tctttctctc aaccatgccc
 61 ctcagggca  cttctgctgg tggtgtgtc  aagcctcctt ttatgggaga atgtggcctc
121 tgtacctttg agtagcaatg agactgatgg ttatccatta tccatcaatg ggctgtttca
181 taatgccatg agactaactt ggaatatcaa aaacctcaac atggaactgc gcaagacata
241 tacagtcaat caagtctctg aaaaattata cgagaactat atgcttgact ttattgagga
301 catggagtat ctggtcaagg ctctcacctg ctgccacaat tattccatca aaactccaga
361 aaacctggac gaagctcaac agattccttt taacgaattt ccaaagctga tcctcagtag
421 aatgtgggct tggaatgaaa cttctaaagt tctactgacc acactccaga gtattccagg
481 aatgcatgat gatgtcattt cattagccaa aaacattgaa acaaaacttg cagagctttt
541 tgagtacacc cagagtatac tcaactcgat ttatggaaca aaatcatct  gatgaagaat ttagtctttt
601 atacaccgtc ttttctggtc ttgaagactt attgcttacg tgtagatata catatggttg aactttatct
661 tgacctttgt aaattttcct attgcttacg tatatgttag tagtgatgtt tgtttatcca aaaatattag
721 caagctatta gagtgtgtgg tatatgttag tagtgatgtt tgtttatcca aaaatattag
781 agatgcttca tgatgctgaa tcttttttaa taatcttaat tttataattg tgaaagtata
841 attgagtata acgagtgtct tttaaaataa aataaacta  tatatat
```

Fig. 12B

SEQUENCE LISTING

<160> NUMBER OF SEQ ID NOS: 4

<210> SEQ ID NO 1
<211> LENGTH: 933
<212> TYPE: DNA
<213> ORGANISM: Mus sp.

<400> SEQUENCE: 1

```
ccacgcgtcc gcaagtgtgc aaggacacct cagagatgcc gctgtctttc actcaaccat      60
gctcctgggc acttctgctg ctggtggtgt caaacctcct tttatgggag aatgtggcct     120
gtctaccttt aagcagcaat gatactgatg atgatccact atccatcaag ggactgttgg     180
atcatgccat gatactttct aagaatatca ctgacctcaa catggagttg cgcaggatat     240
ttaccatcag tgagatgtca gctaaactta ttgataaatt tctaagttca tcatcatcat     300
cagactccta tgatcaattt atgcttgaat ttcttgggca gcaggagtta ctgactaaga     360
acctcaccta ctgccacaaa tactccatca agttcccga agacatagaa gaagcccaaa      420
atgtcatctc tcttgaagac tttccaatct tgatactcag tagaatgcag gcttggaatg     480
aaactctgaa aaaccgaatc aacctatctg aaggtacacc aggaatagac gatgatatcc     540
```

```
tccctatata taaaaatatt gagacaaaaa ttgcagaact tcttgaggac agcaagagta      600
tactcagcca ggcttatgga gcaacagaaa atgtggctga ttacaccctc tggtctggtc      660
ttgaagacct tcaatcatct gatgaagaaa ctcgattttt ggctctttgt aaattatcct     720
attgtttgca tgttgatatc cacacagcta acttttatct ccagttcttg aggtgtgtgg      780
ctcttgttaa tagtgacagc tgcttatctt ccaaaactgg aaatgattca tgatgctgta      840
ttatttaaaa atagtctgat tttatgcatt tcaaagatga gcatgagtaa atgggcatc      900 ttttaaaaga aaataaaca ttgtgtgttt aac                                    933
```

<210> SEQ ID NO 2
<211> LENGTH: 236
<212> TYPE: PRT
<213> ORGANISM: Mus sp.

<400> SEQUENCE: 2

```
Leu Pro Leu Ser Ser Asn Asp Thr Asp Asp Pro Leu Ser Ile Lys
  1               5                  10                  15

Gly Leu Leu Asp His Ala Met Ile Leu Ser Lys Asn Ile Thr Asp Leu
             20                  25                  30

Asn Met Glu Leu Arg Arg Ile Phe Thr Ile Ser Glu Met Ser Ala Lys
         35                  40                  45

Leu Ile Asp Lys Phe Leu Ser Ser Ser Ser Ser Asp Ser Tyr Asp
     50                  55                  60

Gln Phe Met Leu Glu Phe Leu Gly Gln Gln Glu Leu Leu Thr Lys Asn
 65                  70                  75                  80

Leu Thr Tyr Cys His Lys Tyr Ser Ile Lys Val Pro Glu Asp Ile Glu
                 85                  90                  95

Glu Ala Gln Asn Val Ile Ser Leu Glu Asp Phe Pro Ile Leu Ile Leu
            100                 105                 110

Ser Arg Met Gln Ala Trp Asn Glu Thr Leu Lys Asn Arg Ile Asn Leu
        115                 120                 125

Ser Glu Gly Thr Pro Gly Ile Asp Asp Asp Ile Leu Pro Ile Tyr Lys
    130                 135                 140

Asn Ile Glu Thr Lys Ile Ala Glu Leu Leu Glu Asp Ser Lys Ser Ile
145                 150                 155                 160

Leu Ser Gln Ala Tyr Gly Ala Thr Glu Asn Val Ala Asp Tyr Thr Leu
                165                 170                 175

Trp Ser Gly Leu Glu Asp Leu Gln Ser Ser Asp Glu Glu Thr Arg Phe
            180                 185                 190

Leu Ala Leu Cys Lys Leu Ser Tyr Cys Leu His Val Asp Ile His Thr
        195                 200                 205

Ala Asn Phe Tyr Leu Gln Phe Leu Arg Cys Val Ala Leu Val Asn Ser
    210                 215                 220

Asp Ser Cys Leu Ser Ser Lys Thr Gly Asn Asp Ser
225                 230                 235
```

<210> SEQ ID NO 3
<211> LENGTH: 887
<212> TYPE: DNA
<213> ORGANISM: Mus sp.

<400> SEQUENCE: 3

```
ggcagacagg ctgtgccaga actcttcaga gatgtcattt tctttctctc aaccatgccc       60
ctcaggggca cttctgctgg tggtggtgtc aagcctcctt ttatgggaga atgtggcctc      120
```

```
tgtacctttg agtagcaatg agactgatgg ttatccatta tccatcaatg ggctgtttca      180
taatgccatg agactaactt ggaatatcaa aaacctcaac atggaactgc gcaagacata      240
tacagtcaat caagtctctg aaaaattata cgagaactat atgcttgact ttattgagga      300
catggagtat ctggtcaagg ctctcacctg ctgccacaat tattccatca aaactccaga      360
aaacctggac gaagctcaac agattccttt taacgaattt ccaaagctga tcctcagtag      420
aatgtgggct tggaatgaaa cttctaaagt tctactgacc acactcagaa gtattccagg      480
aatgcatgat gatgtcattt cattagccaa aaacattgaa acaaaacttg cagagctttt      540
tgagtacacc cagagtatac tcaactcgat ttatggaaca acaacaacag gaaatgtgga      600
atacaccgtc ttttctggtc ttgaagactt aaaatcatct gatgaagaat ttagtctttt      660
tgacctttgt aaattttcct attgcttacg tgtagatata catatggttg aactttatct      720
caagctatta gagtgtgtgg tatatgttag tagtgatgtt tgtttatcca aaatattag       780 agatgcttca tgatgctgaa tcttttttaaa taatcttaat tttataattg tgaaagtata    840
attgagtata acgagtgtct tttaaaataa aaataaacta tatatat                   887
```

<210> SEQ ID NO 4
<211> LENGTH: 223
<212> TYPE: PRT
<213> ORGANISM: Mus sp.

<400> SEQUENCE: 4

```
Val Pro Leu Ser Ser Asn Glu Thr Asp Gly Tyr Pro Leu Ser Ile Asn
 1               5                  10                  15

Gly Leu Phe His Asn Ala Met Arg Leu Thr Trp Asn Ile Lys Asn Leu
                20                  25                  30

Asn Met Glu Leu Arg Lys Thr Tyr Thr Val Asn Gln Val Ser Glu Lys
            35                  40                  45

Leu Tyr Glu Asn Tyr Met Leu Asp Phe Ile Glu Asp Met Glu Tyr Leu
        50                  55                  60

Val Lys Ala Leu Thr Cys Cys His Asn Tyr Ser Ile Lys Thr Pro Glu
65                  70                  75                  80

Asn Leu Asp Glu Ala Gln Gln Ile Pro Phe Asn Glu Phe Pro Lys Leu
                85                  90                  95

Ile Leu Ser Arg Met Trp Ala Trp Asn Glu Thr Ser Lys Val Leu Leu
            100                 105                 110

Thr Thr Leu Arg Ser Ile Pro Gly Met His Asp Asp Val Ile Ser Leu
        115                 120                 125

Ala Lys Asn Ile Glu Thr Lys Leu Ala Glu Leu Phe Glu Tyr Thr Gln
    130                 135                 140

Ser Ile Leu Asn Ser Ile Tyr Gly Thr Thr Thr Thr Gly Asn Val Glu
145                 150                 155                 160

Tyr Thr Val Phe Ser Gly Leu Glu Asp Leu Lys Ser Ser Asp Glu Glu
                165                 170                 175

Phe Ser Leu Phe Asp Leu Cys Lys Phe Ser Tyr Cys Leu Arg Val Asp
            180                 185                 190

Ile His Met Val Glu Leu Tyr Leu Lys Leu Leu Glu Cys Val Val Tyr
        195                 200                 205

Val Ser Ser Asp Val Cys Leu Ser Lys Asn Ile Arg Asp Ala Ser
    210                 215                 220
```

COMPOSITIONS, KITS, AND METHODS FOR MODULATING SURVIVAL AND DIFFERENTIATION OF MULTI-POTENTIAL HEMATOPOIETIC PROGENITOR CELLS

CROSS-REFERENCE TO RELATED APPLICATIONS

This application is entitled to priority pursuant to 35 U.S.C. §119(e) to U.S. provisional patent application 60/141,060, which was filed on Jun. 25, 1999, and to U.S. provisional patent application 60/162,472, which was filed on Oct. 29, 1999.

STATEMENT REGARDING FEDERALLY SUPPORTED RESEARCH OR DEVELOPMENT

This research was supported in part by U.S. Government funds (National Institutes of Health grant number RO1 HD24518 and U.S. Army Breast Cancer Program Grant No. DAMD 17-98-1-8327), and the U.S. Government may therefore have certain rights in the invention.

BACKGROUND OF THE INVENTION

The invention relates generally to the field of maintaining and expanding populations of hematopoietic cells ex vivo.

Blood cells of all types derive from hematopoietic progenitor cells, which are multipotential (i.e., capable of differentiating into any of a variety of types of blood cells) at early stages of development. At later stages of development, a hematopoietic progenitor cell can become one of only certain types of cells, depending on the developmental path the cell has undergone. By way of example, a hematopoietic stem cell can differentiate to become either a myelo-erythroid progenitor cell or a lymphoid stem cell. If the cell becomes a myelo-crythroid progenitor cell, it can become an erythroid progenitor (and subsequently an erythrocyte) or a myeloid progenitor cell. A myeloid progenitor cell, in turn, can differentiate to become a megakaryocyte (MK), or one of several other types of blood cells. Platelets are derived from MKs. Thus, MKs and the physiological processes by which hematopoietic progenitor cells differentiate into MKs are involved in disorders associated with aberrant formation and activation of platelets.

Many pregnancy-associated diseases (e.g., pregnancy-induced hypertension, pre-eclampsia, and diabetes) result from aberrant modulation of maternal physiology. For example, although the platelet count has been observed to decrease slightly during human pregnancy in some studies (Fay et al., 1983, Obst. Gynecol. 61:238–240), the rate of platelet production apparently increases to compensate for the dramatic increase in blood volume during pregnancy (Davison et al., 1989, Baillieres Clin. Endocrinol. Metab. 3:451–472). Aberrantly high rates of platelet activation in plasma have been clinically associated with pre-eclampsia, and anti-platelet treatment is widely used to treat pregnant women afflicted with this disorder (Beaufils et al., 1985, Lancet 1:840–842; Steyn et al., 1997, Lancet 350:1267–1271; Konijnenberg et al., 1997, Am. J. Obst. Gynecol. 176:461–469). Disorders associated with aberrantly low rates of platelet production include thrombocytopenia (e.g., that associated with leukemia and alcohol-induced thrombocytopenia).

Several cytokines, including thrombopoietin (TPO), interleukin-6 (IL-6), IL-11, leukemia inhibitory factor, and kit ligand, have been demonstrated to enhance MK maturation under normal physiological conditions (Baatout, 1998, Anticancer Res. 18:1871–1882; Ellis et al., 1995, Blood Rev. 9:1–6).

It is not understood, which factor or combination of factors are responsible for pregnancy-associated thrombopoietic activity. Thus, efficacious treatment of pregnancy-associated thrombopoietic disorders has been hampered. A significant need remains for methods which can be used to treat such disorders.

Ex vivo expansion of hematopoietic progenitor cells and transplantation of those cells have several important clinical uses, including stem cell rescue following myeloablative therapy and gene therapy. However, there is presently no clinically approved method to preserve and expand hematopoietic progenitor cells, particularly at their earliest, most multi-potential stages. The most common approach to ex vivo multi-potential hematopoietic cell expansion is to culture purified progenitor cells (i.e., those expressing the CD34 marker) in the presence of early-acting cytokines such as interleukin-3. Unfortunately, using prior art cell expansion methods, there is generally an inverse relationship between cell proliferation and the percentage of primitive stem cells which are maintained in a relatively non-differentiated stage of development. Thus, using prior art methods, when hematopoietic progenitor cells are induced to proliferate or differentiate, early progenitor cells are lost. Because these early cells can be the most useful for inducing hematopoietic engraftment (i.e., in that survival of these cells in vivo can provide a source for many or all blood cell types), differentiation associated with prior art cell expansion methods represents a significant shortcoming of those methods.

Recent work has shown that inclusion, in a nutritive medium for maintaining hematopoietic progenitor cells ex vivo, of a combination of thrombopoietin (TPO), stem cell factor (SCE), and flt3 ligand (Flt-3L; i.e., the ligand of the flt3 gene product) was useful for expanding primitive (i.e., relatively non-differentiated) human hematopoietic progenitor cells in vitro, and that those cells were capable of engraftment in SCID-hu mice (Luens et al., 1998, Blood 91:1206–1215). Nonetheless, a significant need remains for other methods for expanding multi-potential hematopoietic progenitor cells in a manner that preserves a population of the cells at an early stage of their differentiation/development.

The present invention provides compositions, kits, and methods which satisfy one or more of the needs described above.

BRIEF SUMMARY OF THE INVENTION

The invention includes a method of maintaining mammalian (e.g., human) hematopoietic progenitor cells in vitro. This method comprises maintaining the cells in vitro in a nutritive medium (e.g., for minutes, hours, or 3, 6, 9, 13, or more days) comprising murine prolactin-like protein E (mPLP-E) or murine prolactin-like protein F (mPIP-F; collectively mPLP-E/F). The mPLP-E/F can, for example, have the amino acid sequence SEQ ID NO: 2, and can be glycosylated at one or more of residues 6, 28, 80, 119, 127, and 234 of SEQ ID NO: 2. The nutritive medium can further comprise a cytokine selected from the group consisting of thrombopoietin, interleukin-3, interleukin-6, interleukin-11, leukemia inhibitory factor, kit ligand, stem cell factor, and flt3 ligand. The cells can, for example, be cells obtained from bone marrow, fetal cells, or cells obtained from cord blood. Use of this method can result in expansion of the cells. This method can also be used to induce proliferation, differentiation, or both, of mammalian hematopoietic progenitor cells in vitro.

The invention also includes a method of inhibiting differentiation of mammalian hematopoietic progenitor cells. This method comprises contacting the cells (e.g., in vitro) with an antibody substance which specifically binds with mPLP-E/F. In an alternative embodiment, the cells are contacted with an antibody substance which specifically binds with a cell surface receptor of the cells and which inhibits binding of mPLP-E/F with the receptor.

The invention further includes a method of inducing proliferation of mammalian hematopoietic progenitor cells. This method comprises contacting the cells with an antibody substance which inhibits binding of one of mPLP-E and mPLP-F with a receptor on the cells without significantly inhibiting an activity normally associated with binding of mPLP-E or mPLP-F with the receptor.

In another aspect, the invention includes a method of assessing whether a test compound is useful for modulating either of proliferation and differentiation of mammalian hematopoietic progenitor cells. This method comprises maintaining the cells in vitro in a nutritive medium comprising mPLP-E (or mPLP-F) and in the presence and absence of the test compound, whereby a difference between proliferation or differentiation of the cells in the presence of the test compound and proliferation or differentiation of the cells in the absence of the test compound is an indication that the test compound is useful for modulating proliferation or differentiation of mammalian hematopoietic progenitor cells.

BRIEF DESCRIPTION OF THE DRAWINGS

FIG. 3, comprising FIGS. 3A–3D, is a quartet of images which depict the morphology and AchE-staining intensity of MK colonies formed in semi-solid cultures. MK colonies were derived from murine primary bone marrow cultures which were treated with IL-3 alone (FIG. 3A), with both IL-3 and GST (FIG. 3B), with both IL-3 and GST-mPLP-E (FIG. 3C), or with both IL-3 and TPO (FIG. 3D). The scale bar in each image represents 100 micrometers.

FIG. 7, comprising FIG. 7A depicts the frequency of CD34$^+$ cells in the cultures.

FIG. 7B depicts the frequency of CD34$^+$/CD41$^+$ cells in the cultures. FIG. 7C depicts the degree of CD34$^+$ cell expansion, relative to the number of CD34$^+$ cells seeded at day 0. FIG. 7D depicts the ratio of CD34$^+$/CD41$^+$ cells to the number of CD34$^+$ cells seeded at day 0 (i.e., the number of CD34$^+$/CD41$^+$ cells produced per initially seeded CD34$^+$ cell).

FIG. 8, comprising FIGS. 8A and 8B, is a pair of graphs which depict the effect of medium cytokine composition on CD41 marker expression in cells derived from CD34$^+$ cells purified from human bone marrow in cell cultures maintained in the presence of medium comprising mPLP-E (filled circles), TPO (open circles), both (half-filled circles), or neither (crosses). FIG. 8A shows the frequency of CD41$^+$ expression in the cultures. FIG. 8B depicts the number of CD41$^+$ cells produced per initially seeded CD34$^+$ cell.

FIG. 9, comprising FIGS. 9A through 9H, is a set of graphs which depict the effect of medium cytokine composition on human hematopoietic progenitor cell colony formation in cells derived from CD34$^+$ cells purified from human bone marrow in cell cultures maintained in the presence of medium comprising mPLP-E (filled circles), TPO (open circles), both (half-filled circles), or neither (crosses). FIGS. 9A, 9C, 9E, and 9G show the frequency of CFU-MK, BFU-E, CFU-GEMM, and CFU-GM, respectively, in the cultures. FIGS. 9B, 9D, 9F, and 9H depicts fold expansion of CFU-MK, BFU-E, CFU-GEMM, and CFU-GM, respectively, in the cultures.

FIG. 11, comprising FIGS. 11A and 11B, lists the amino acid sequence (SEQ ID NO: 2; FIG. 11A) of mature murine prolactin-like protein E (mPLP-E) and the nucleotide sequence (SEQ ID NO: 1; FIG. 11B) which encodes it.

FIG. 12, comprising FIGS. 12A and 12B, lists the amino acid sequence (SEQ ID NO: 4; FIG. 12A) of mature murine prolactin-like protein F (mPLP-F) and the nucleotide sequence (SEQ ID NO: 3; FIG. 12B) which encodes it.

DETAILED DESCRIPTION OF THE INVENTION

Figure 1:
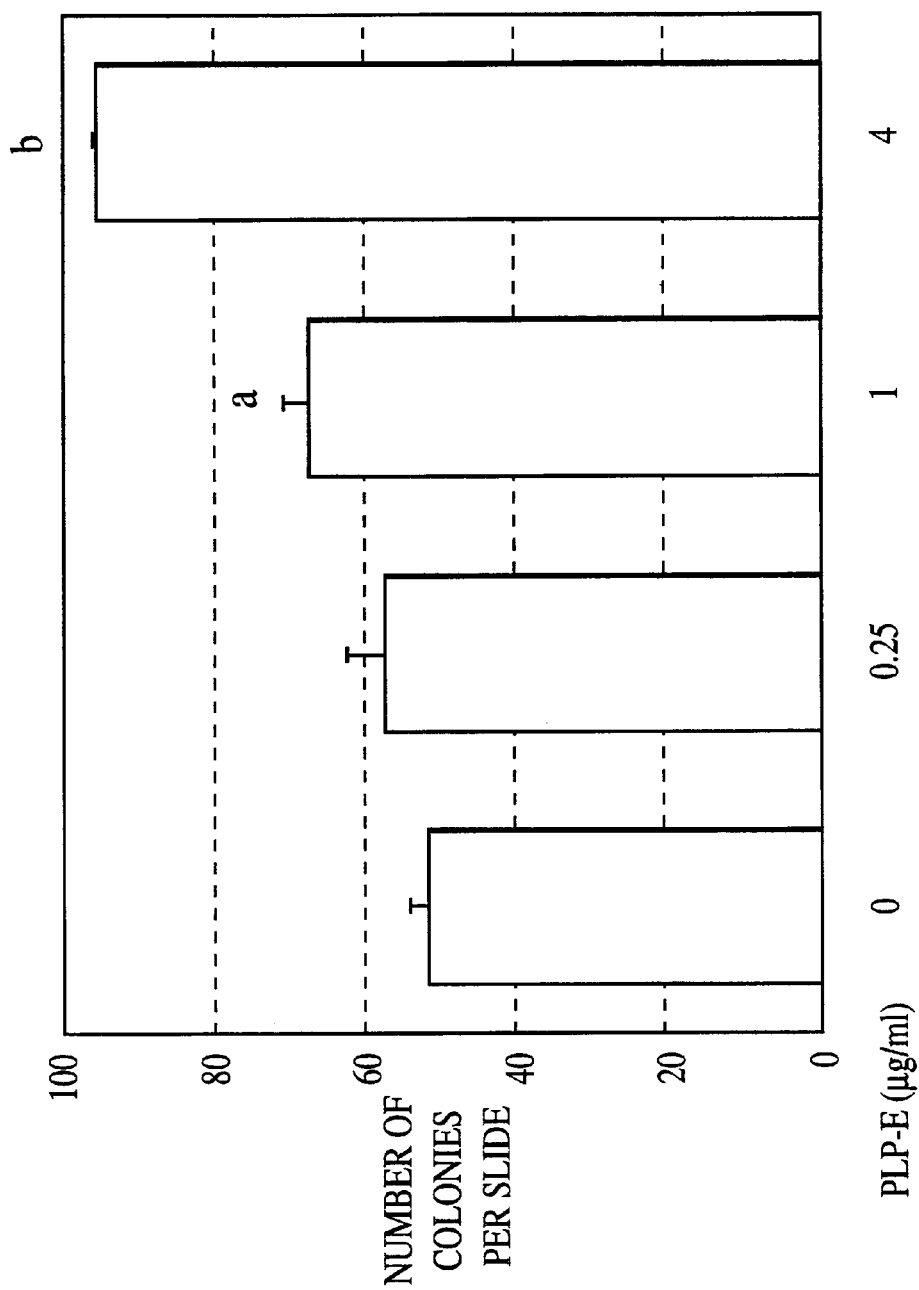
FIG. 1 is a bar graph which indicates the dose response of mPLP-E on murine CFU-MK formation, as described herein. Results shown are duplicate assays with the observed variation. Data were evaluated by a one-way analysis of variance followed by a Tukey's test. a, versus control, p<0.05; b, versus control, p<0.01.

The invention is based on the discovery that a previously-described placental glycoprotein hormone of the murine prolactin family, namely murine prolactin-like protein E (mPLP-E), can enhance survival of mammalian (i.e., both murine and non-murine mammalian, including human) multi-potential hematopoietic progenitor cells. mPLP-E can furthermore induce expansion of hematopoietic precursor cells of megakaryocytic and erythroid lineages (e.g., megakaryocytes and erythropoietic cells). mPLP-E is capable of binding mammalian (e.g., murine and human) hematopoietic precursor cells by means of a specific cell-surface receptor. mPLP-E also enhances murine MK differentiation through a gp130-dependent signaling pathway. The properties of mPLP-E indicate that it can be involved in pregnancy-associated hematopoietic disorders and other disorders associated with aberrant MK development or aberrant platelet production.

The invention in further based on the discovery that another previously-described placental glycoprotein hormone of the murine prolactin family, namely murine prolactin-like protein F (mPLP-F), exhibits similar receptor binding properties and similar activities.

Definitions

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

A "nutritive medium" is a liquid, semi-solid, or solid substrate within which or in contact with which a mammalian hematopoietic progenitor cell (e.g., a $CD34^+$ cell) is able to remain viable for a period of at least a few hours.

The terms "antibody" and "antibody substance" as used interchangeably herein refer to immunoglobulin molecules and immunologically active portions of immunoglobulin molecules, i.e., molecules that contain an antigen binding site which specifically binds an antigen, such as a polypeptide of the invention. A molecule which specifically binds to a given polypeptide of the invention is a molecule which binds the polypeptide, but does not substantially bind other molecules in a sample, e.g., a biological sample, which naturally contains the polypeptide. Examples of immunologically active portions of immunoglobulin molecules include F(ab) and $F(ab')_2$ fragments which can be generated by treating the antibody with an enzyme such as pepsin. The invention provides polyclonal and monoclonal antibodies. The term "monoclonal antibody" or "monoclonal antibody composition", as used herein, refers to a population of antibody molecules that contain only one species of an antigen binding site capable of immunoreacting with a particular epitope.

Description

The amino acid sequences of murine placental prolactin-like proteins F and F (mPLP-E and mPLP-F) and the nucleotide sequences encoding them have been previously described by the inventors (Lin et al., 1997, Endocrinology 138:5535–5540). At the time those sequences were discovered, no biological or physiological function could be assigned to either protein.

The present invention is based on the discovery that each of these two proteins can modulate survival and maturation/differentiation of multi-potential hematopoietic progenitor cells. Furthermore, the activities associated with these two proteins are not limited to mice (i.e., in which mPLP-E and mPLP-F were discovered). Instead, mPLP-E and mPLP-F appear to prolong survival, proliferation, differentiation, or some combination thereof, in both human and murine progenitor cells, and presumably in all mammalian hematopoietic progenitor cells of the megakaryocytic and erythroid lineages.

The invention includes a method of maintaining mammalian (e.g., human or murine) hematopoietic progenitor cells in vitro (or ex vivo) in a state in which the relatively immature character (i.e., non-differentiated and not committed to become particular types of blood cells or to become cells of a particular hematopoietic lineage) at least a portion of the progenitor cells is prolonged. Prolongation of the pluripotence of the progenitor cells is effected by maintaining the cells in a nutritive medium comprising one or both of mPLP-E and mPLP-F. The nutritive medium can, optionally, be replaced or replenished from time to time (e.g., every 12–72 hours) or continuously. The concentration of mPLP-E or mPLP-F in the nutritive medium should be at least about 100 nanograms per milliliter, although concentrations of at least about 1 microgram per milliliter or about 5 micrograms per milliliter are preferred. Higher concentrations can also be used. If the mPLP-E or mPLP-F protein is glycosylated (e.g., at one or more glycosylation site identified herein), then concentrations lower than 100 nanograms per milliliter (c.g., concentrations of 50, 20, 10, 5, 2, or 1 nanogram per milliliter) can be used.

The composition of the nutritive medium is, apart from the presence of the progenitor cells and the mPLP-E (and/or mPLP-F), not critical. Substantially any medium that is suitable for maintaining hematopoietic progenitor cells in vitro for a period of hours, days, or weeks can be used. Many such cell culture media are known in the art. Furthermore, the source of the hematopoietic progenitor cells is not critical. Preferably, the cells are obtained from a tissue or body location at which multi-potential hematopoietic progenitor cells are plentiful (e.g., bone marrow obtained from pelvis or sternum of adult mammals or cells obtained from fetal liver or spleen tissues). Another source of multi-potential hematopoietic progenitor cells is 'cord blood' (i.e. blood cells obtained from the placenta or umbilicus of a mammal at, or shortly following birth), which can optionally be stored in a frozen state. The compositions, kits, and methods described herein can be used to modulate survival and differentiation of multi-potential hematopoietic progenitor cells obtained from tissues in which such cells are relatively sparse (e.g., whole blood).

The invention includes a composition comprising a nutritive medium useful for enhancing proliferation, differentiation, or both, of mammalian hematopoietic progenitor cells, as described herein. The composition comprises one or more components of a nutritive medium (preferably a complete medium, such as Dulbecco's modified Eagle's medium) and one or both mPLP-E and mPLP-F. The medium can comprise serum (e.g., fetal bovine serum), or it can be serum-free. The concentration of mPLP-E/F is, as described above, preferably at least about 100 nanograms per milliliter, and is more preferably at least 1 or 5 micrograms per milliliter. The composition can be packaged or prepared in the form of a kit comprising one or more components of a nutritive medium and at least one mPLP-E or mPLP-F protein. The kit can be used to prepare a nutritive medium which comprises at least one of mPLP-E and mPLP-F and which can be used as described herein. The kit can further include an instructional material which described making such a composition or its use in a method described herein.

The hematopoietic progenitor cells can be maintained in the nutritive medium for a period of minutes, days, or even weeks. When the cells are being maintained for the purpose of expanding their number, the cells are preferably maintained in the presence of mPLP-E or mPLP-F for a period of at least about 3 days, although they can be maintained longer (e.g., for 6, 9, 13, or more days).

One important use of the methods described herein for maintaining mammalian hematopoietic progenitor cells in vitro is culture and expansion of the cells ex vivo. That is, progenitor cells are obtained from a mammal and maintained in vitro prior to returning the cells to the mammal from which they were obtained or prior to injecting them into another mammal of the same species as that of the mammal from which they were obtained or into another mammal of a different species. The cells can be modified in vitro prior to injecting the cells into the mammal (e.g., by contacting the cells with a gene vector such as an adenovirus vector, naked DNA, or DNA complexed with a transformation-inducing agent such as polylysine). Alternatively, the progenitor cells can be induced to proliferate, to differentiate, or to both proliferate and differentiate, as described herein.

Proliferation of mammalian hematopoietic progenitor cells in vitro can be induced using any of a variety of known agents and combinations of agents. For example, interleukins-(ILs-)11 and 3, thrombopoietin (TPO), stem cell factor (SCF), and flt3 ligand are all known to induce proliferation of one or more types of hematopoietic progenitor cells in mammals. A shortcoming of prior art methods of inducing proliferation of mammalian hematopoietic progenitor cells in vitro is that those methods often lead to depletion of multi-potential progenitor cells. Thus, although known methods can be used to increase the numbers of blood cells and committed blood cell precursors in vitro, prior art methods exhibit limited ability to maintain multi-potential cells among those cells and precursors. As a result, blood cell populations expanded in vitro (or ex vivo) using prior methods have limited capacity for restoring the hematopoietic system of a mammal (e.g., an irradiated human) in which the hematopoietic system has been ablated or depleted, either intentionally or as an outcome of a disease.

As described herein, maintaining mammalian multi-potential hematopoietic progenitor cells in medium comprising mPLP-E or mPLP-F enhances survival of multi-potential cells among proliferating progenitor cells. Thus, the invention includes an improvement to prior in vitro methods for maintaining multi-potential hematopoietic progenitor cells in culture and for increasing the numbers of such multi-potential cells among expanded cell populations. This improvement comprises including one or both of mPLP-E and mPLP-F in the nutritive medium in which the progenitor cells are maintained or expanded. Of course, combinations of mPLP-E (or mPLP-F) and other cytokines can be used. For example, it can be advantageous to include both mPLP-E and TPO in the nutritive medium, particularly where enhancement of survival of multi-potential cells of megakaryocytic and erythroid lineages is desired. Such medium can also be supplemented with one or more of IL-11, SCF, and Flt3 ligand.

Furthermore, as described herein, mPLP-E can be used in vitro to enhance differentiation of multi-potential hematopoietic progenitor cells into megakaryocytic cells, at least among murine hematopoietic progenitor cells, and presumably in hematopoietic progenitor cells of other mammals. In order to effect differentiation into megakaryocytic cells, mPLP-E can be used under the same conditions, and at about the same concentrations, as described herein for enhancing survival of hematopoietic progenitor cells in vitro. Thus, when used in this manner, mPLP-E can both enhance survival of at least a portion of multi-potential hematopoietic progenitor cells and enhance differentiation of another portion of the progenitor cells into megakaryocytic cells.

Numerous cytokines (e.g., TPO, IL-6, IL-11, leukemia inhibitory factor, ciliary neurotrophic factor, and kit ligand) are also known to enhance differentiation of mammalian multi-potential hematopoietic progenitor cells into megakaryocytic cells. mPLP-E (or mPLP-F) can be used in combination with one or more of these cytokines in order to enhance differentiation into megakaryocytes (and thence into platelets). Furthermore, mPLP-E/F, a differentiation-enhancing cytokine, and a proliferation-enhancing cytokine can be used in combination to both enhance proliferation of hematopoietic progenitor cells and increase the proportion of megakaryocytic cells in the expanded population.

mPLP-E can induce megakaryocytes to differentiate into plasma cells when the mPLP-E are contacted (i.e., either in vivo or for a selected period {e.g., minutes, hours, or days} in vitro). The invention thus includes a method of inducing mammalian megakaryocytes to differentiate into platelets, the method comprising contacting the megakaryocytes with mPLP-E. When the megakaryocytes are contacted with mPLP-F in vitro, the megakaryocytes (or platelets derived therefrom) can be stored, returned to the mammal from which the megakaryocytes were obtained, or provided to a different mammal of the same or different species. The megakaryocytes or platelets can, optionally, be separated from some or substantially all blood cells of other types prior to storage or infusion.

As described and exemplified herein, mPLP-E and mPLP-F are capable of enhancing proliferation and differentiation (at least under certain circumstances) of multi-potential mammalian hematopoietic progenitor cells in vitro. The invention thus includes an in vitro method of screening compounds which interfere with progenitor cell proliferation and differentiation in vivo. As noted herein, mPLP-E and mPLP-F exert their effects on progenitor cells by interacting with a cell-surface receptor of such cells. Thus, the in vitro methods described herein for enhancing proliferation and differentiation of hematopoietic progenitor cells can be used to assess whether a test compound interferes with these processes. This assessment is performed by performing duplicate assessments of proliferation or differentiation, wherein one duplicate assessment is performed in the presence of the test compound and the other duplicate assessment is performed in the absence of the test compound. If a lesser degree of proliferation or differentiation occurs in the presence of the test compound than in its absence, then this is an indication that the test compound is an inhibitor of proliferation or differentiation of the mammalian hematopoietic progenitor cells used in the assessments. These methods are useful for identifying compounds that can be used to inhibit (or even abolish) proliferation of the progenitor cells in vitro or in vivo. The methods are also useful for identifying compounds that are can be used (again, either in vitro or in vivo) to inhibit (or even abolish) differentiation of the progenitor cells into cells of one or more types or hematopoietic lineages.

One class of compounds that are contemplated to be useful for inhibiting proliferation or differentiation of the mammalian hematopoietic progenitor cells are antibody substances which bind with a cell-surface receptor of hematopoietic progenitor cells with which mPLP-E or mPLP-F interact and which prevent such interaction. Without being bound by any particular theory of operation, such antibody substances are believed to prevent interaction of the receptor and its physiological substrate, even if that substrate is different than mPLP-E/F. Progenitor cell proliferation and differentiation associated with interaction of the receptor with its physiological ligand are thereby inhibited.

Such antibody substances can be identified by, for example, screening libraries of antibody substances having randomly-generated complementarity determining regions or by screening libraries of antibody substances raised (i.e., using standard antibody generation methods) against progenitor cells or proteins thereof.

Antibody substances which are raised against (i.e., which bind specifically with) a receptor with which mPLP-E or mPLP-F binds (i.e., thereby preventing binding of the mPLP protein therewith) can activate the receptor, thereby wholly or partially mimicking the effect of binding of the mPLP protein with the receptor. Such antibody substances can be used in place of mPLP-E or mPLP-F. Antibody substances capable of activating a receptor with which an mPLP protein binds can be identified by their ability to inhibit mPLP-E/F binding with the receptor (e.g., as assessed by lack of binding of a detectably labeled mPLP protein with the receptor or a cell bearing the receptor) without abolishing (or significantly inhibiting) an activity normally associated with mPLP-E/F binding with the receptor (e.g., without abolishing mammalian hematopoietic progenitor cell differentiation normally associated with mPLP-E/F binding).

The mPLP-E and mPLP-F proteins used in the compositions, kits, and methods described herein are preferably those described in Lin et al. (1997, Endocrinology 138:5535–5540) and depicted herein in FIGS. 11 and 12, respectively. However, it is recognized that variants of these proteins can be used, so long as the variations in the molecules do not significantly interfere with their function. Interference with function can be detected, for example, using the assay methods described herein. It is known that conservative amino acid substitutions can be made in proteins, generally without affecting their properties. For example, conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. As described herein, the progenitor cell proliferation- and differentiation-enhancing properties of mPLP-E and mPLP-F appear to be substantially non-affected by the glycosylation state of the protein. Thus, these proteins can be glycosylated at none, or at one or more, of the putative glycosylation sites identified in the Lin et al. reference (i.e., at one or more of residues 6, 28, 80, 119, 127, and 234 of SEQ ID NO: 2 for MPLP-E and at one or more of residues 6, 73, and 105 of SEQ ID NO: 4 for mPLP-F). Also embraced are sequences which have phosphorylated amino acid residues, e.g., phosphotyrosine, phosphoserine, or phosphothreonine. The amino acid residues indicated in the Lin et al. reference as being conserved between mPLP-E and mPLP-F are preferably present in the protein used in the compositions, kits, and methods described herein.

The invention is now described with reference to the following Examples. These Examples are provided for the purpose of illustration only and the invention is not limited to these Examples, but rather encompass all variations which are evident as a result of the teaching provided herein.

EXAMPLE 1

Induction of Megakaryocyte Differentiation by a Novel Pregnancy-Specific Hormone Maturation of megakaryocytes and subsequent platelet release are normally regulated by a network of cytokines, including thrombopoietin and various interleukins. Because abnormal platelet production and activation have been implicated in gestational pathologies, additional pregnancy-specific cytokines can have important roles in regulation of megakaryocytopoiesis. The hormone prolactin-like protein E (PLP-E), a murine placental hormone that has recently been described, binds with megakaryocytes by means of a specific cell surface receptor and induces megakaryocyte differentiation by means of a gp130-dependent signal transduction pathway.

A murine placental hormone (designated murine prolactin-like protein E; mPLP-E) has been identified, which is expressed at high levels at mid-gestation in mice (Lin et al., 1997, Endocrinology 138:5535–5540; Muller et al., 1998, Biochim. Biophys. Acta 1396:251–258). The experiments presented in this example demonstrate that mPLP-E binds with mouse MK cells at a specific cell-surface receptor, and that mPLP-E enhances murine MK differentiation by way of a gp130-dependent signaling pathway. The results of these experiments indicate that mPLP-E contributes to the pregnancy-associated MK development and platelet production.

The materials and methods used in the experiments presented in this example are now described Preparation of Fusion Proteins cDNA encoding mPLP-E was linked in-frame with a secreted alkaline phosphatase (AP) gene in a mammalian expression vector, as described (Muller et al., 1998, J. Histochem. Cytochem. 46:737–743). Fusion protein was obtained by transient transfection of the resulting DNA construct into Chinese hamster ovary cells and subsequent collection of culture medium over a 2-day period. Medium containing secreted AP-mPLP-E was concentrated and used in binding assays. mPLP-E not fused with the AP protein partner was generated using a similar approach and used as a competitor in binding experiments. The CDNA encoding mPLP-E was also fused with a glutathione-s-transferase (GST) coding sequence to produce GST-mPLP-E fusion protein, which was expressed in and purified from bacteria prior to use.

Hormone Binding Assay

Tissue sections were prepared and binding assays were performed essentially as described (Muller et al., 1998, J. Histochem. Cytochem. 46:737–743). Briefly, tissue sections were pre-incubated with an appropriate competitor for 30 minutes at room temperature before incubating with AP-mPLP-E for 45 minutes. Slides were washed briefly in Hanks' balanced salt solution three times and fixed in a solution containing 20 millimolar HEPES buffer (pH 7.4), 60% (v/v) acetone, and 3% (v/v) formaldehyde. After inactivating endogenous AP by maintaining the slides at 65° C. for 30 minutes, the enzymatic activity derived from the fusion protein was detected by a chromogenic reaction. In some experiments, adjacent sections were also stained for acetylcholinesterase (AchE) activity or with a monoclonal antibody (described in Shavit et al., 1998, Genes Dev. 12:2164–2174) that binds specifically with CD41. Images were captured using a digital camera.

Colony Formation Assay

Femurs from CD1 female mice were flushed with 5 milliliters of Iscove's modification of Dulbecco's medium containing 10% (v/v) fetal bovine serum (Life Technologics, Inc.). The marrow cells obtained thereby were passed through 19 and 25 gauge needles sequentially and cultured at 37° C. for 45 minutes in order to remove attached stromal cells. The cells were washed with Iscove's modification of Dulbecco's medium containing 1% (v/v) NUTRIDOMA™ (Roche Diagnostics Corporation, Indianapolis, Ind.) and plated in semi-solid medium for colony formation assays or in liquid medium for flow cytometric analysis. Colony formation assays were performed using MEGACULT™ medium (Stem Cell Technology, Vancouver, Canada) following instructions provided by the manufacturer. About $5 \times 10^5$ nucleated bone marrow cells were cultured for 5–6 days in each well of 2-well chamber slides. Typically, 10 nanograms per milliliter murine IL-3, 15 nanograms per milliliter murine IL-6, 50 nanograms per milliliter murine TPO, and 4 micrograms per milliliter GST or GST-mPLP-E were included in the culture media. In some experiments, a mixture of monoclonal antibodies (RX187 and RX435) which bind specifically with gp130 (as described; Nyui et al., 1998, Biochem. Biophys. Res. Commun. 245:928–932) was added to the culture media at a concentration of 5 micrograms per milliliter. Colonies were dried and stained for AchE activity before processing for microscopy and colony scoring. An MK colony was defined as at least three clustered, positively-stained cells.

Flow Cytometric Analysis

About $5 \times 10^6$ bone marrow cells were cultured in the presence of 3 nanograms per milliliter IL-3 in the presence or absence of 2 micrograms per milliliter GST-mPLP-E for 4–5 days. Cells were harvested and stained with fluorescein isothiocyanate-(FITC-)labeled anti-mouse CD41 antibody (Pharmingen, San Diego, Calif.) for 60 minutes on ice. Cells were washed three times with cold phosphate-buffered saline and re-suspended in a 0.1% citrate solution containing 50 micrograms per milliliter propidium iodide for 30 minutes before the addition of RNase to a final concentration of 20 micrograms per milliliter, as described (Jackson et al., 1984, Blood 63:768–778). Samples were stored at room temperature for 30 minutes in the dark before analysis using a FACSCALIBUR™ (Becton Dickinson, Franklin Lakes, N.J.) flow cytometry system. A mouse erythroleukemia cell line (GM979) was used as a ploidy control.

Immunoblot Analysis

A polyclonal antiserum against mPLP-E was generated by immunization of rabbits with bacterially derived GST-mPLP-E. Plasma samples from pregnant mice were collected on day 10 of gestation in containers containing lithium heparin (Becton Dickinson). Samples were separated by electrophoresis through 10% (w/v) polyacrylamide gels in the presence of SDS and transferred to nitrocellulose membranes. After incubating in blocking buffer (20 millimolar Tris (pH 7.6), 150 millimolar NaCl, 0.5% Triton X-100, and 5% nonfat milk), the antiserum was added at 1:2000 dilution. After washing in blocking buffer, membranes were incubated with a secondary antibody (horseradish peroxidase-conjugated anti-rabbit IgG) and processed for film exposure.

The results of the experiments presented in this Example are now described.

mPLP-E Binds Specifically with Murine MK Cells

To identify potential physiological targets for mPLP-E action, an AP-mPLP-E fusion protein was used as a probe to search for hormone binding sites in pregnant mouse tissues. AP-mPLP-E binding was observed in most hematopoietic tissues, including fetal liver, maternal bone marrow, and maternal spleen. Two distinct binding targets were identified in the spleen: large cells with multi-lobulated nuclei and abundant cytoplasm (i.e., characteristics of MK cells), and smaller binding targets that may correspond to MK cell fragments, (e.g., platelets). To confirm the identity of the large cells, adjacent spleen sections were prepared and stained for AchE, an enzymatic marker for the MK lineage. AchE activity co-localized to the cells that bound AP-mPLP-E. In addition, a monoclonal antibody (i.e., anti-CD41) that reacts with mouse glycoprotein IIb (an MK-specific cell surface integrin) also recognized cells with which mPLP-E bound. Tissues obtained from non-pregnant female and male mice displayed similar binding patterns for the fusion protein. Therefore, although synthesis of mPLP-E is restricted to murine placenta during early gestation, the sites on MK cells to which mPLP-E binds are not expressed in a pregnancy-specific manner. Thus, mPLP-E can be bound with MKs in both pregnant and non-pregnant mice.

Addition of excess mPLP-E completely eliminated binding of AP-mPLP-E with MKs. Another prolactin-related placental hormone, murine PLP-B, was unable to block AP-mPLP-E binding with MK cells. Thus, binding of mPLP-E with MK cells is saturable and specific, which indicates that mPLP-E specifically binds with an MK cell surface receptor. The observation that bacterially derived fusion protein, GST-mPLP-E, at a concentration of 10 micrograms per milliliter effectively competed with mPLP-E for MK cell-surface binding sites indicates that specific binding of mPLP-E with MK cells is independent of the glycosylation state of mPLP-E.

mPLP-E Enhances Murine MK Cell Differentiation

Because GST-mPLP-E is capable of receptor binding and could be readily purified in large amounts, this fusion protein was used to examine mPLP-E activity. In a semi-solid culture, GST-mPLP-E induced primary mouse bone marrow MK differentiation, as indicated by increased MK cell size and enhanced AchE staining. This effect was comparable to MK cell size and AchE staining associated with MK cell treatment with either IL-6 or TPO (i.e., known enhancers of murine MK cell differentiation).

In order to assess induction of MK differentiation quantitatively, semi-solid primary mouse bone marrow cell cultures were supplemented with GST-mPLP-E and interleukin-3 (IL-3). IL-3 is a cytokine known to be capable of inducing proliferation of multiple hematopoietic lineages, including MK progenitors. GST-mPLP-E induced a dose-dependent increase in colony-forming units-megakaryocyte (CFU-MK), with significant effects observable at GST-mPLP-E concentrations of 1 and 4 micrograms per milliliter, as indicated in FIG. 1. Although the effective doses of GST-mPLP-E are higher than the optimal concentrations for IL-6 or TPO in this assay, these concentrations of mPLP-E are comparable with the maternal plasma concentration of mPLP-E during pregnancy, as assessed by semi-quantitative immunoblotting and comparison with purified GST-mPLP-E standards.

Figure 2:
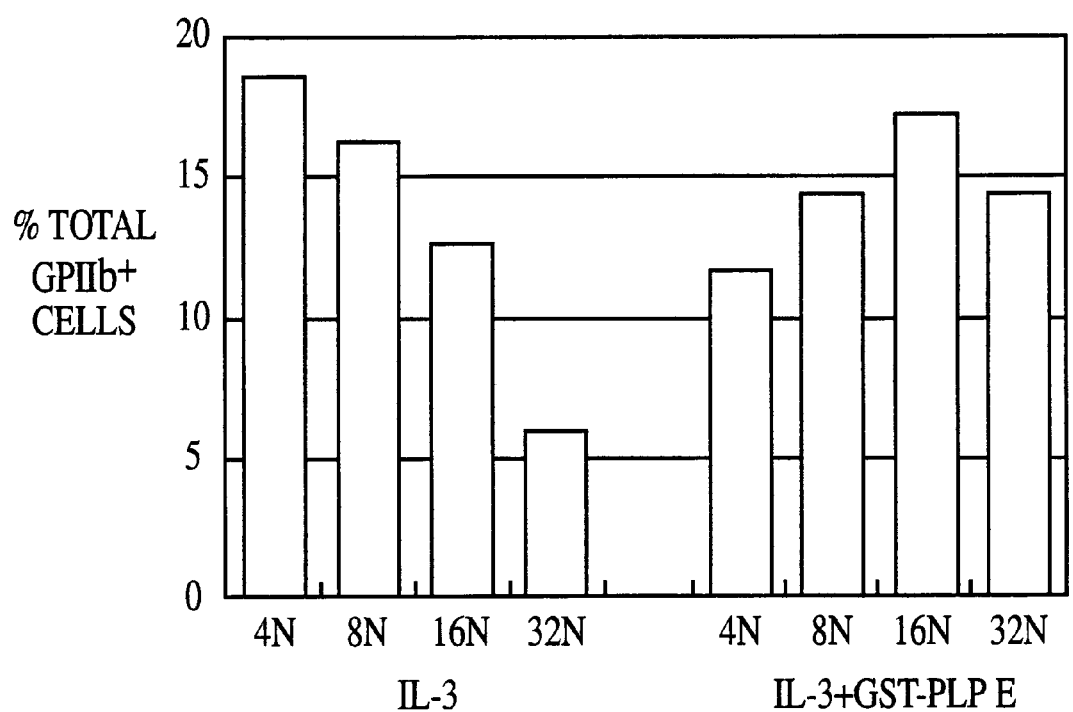
FIG. 2 is a bar graph which depicts the results of two-color flow cytometric analysis of murine MK (i.e., GPIIb$^+$) cells. The bar graph indicates the distribution of MK cells having the indicated DNA contents following treatment with IL-3 alone or with IL-3 and GST-mPLP-E. In the axis legend, "GPIIb" means glycoprotein IIb.

In addition to quantifying the effect of mPLP-E based on colony formation, two-color flow cytometric analysis indicated that the addition of GST-mPLP-E together with IL-3 in liquid medium cultures significantly shifted MK ploidy toward higher numbers, as shown in FIG. 2. The majority of glycoprotein IIb-positive cells had a DNA content less than 8N in cultures treated only with IL-3. However, addition of GST-mPLP-E resulted in a higher percentage of MK cells with a DNA content of 16N and 32N. The 16N/32N cell population accounts for 31% of all gated cells in the cultures treated with the combination of IL-3 and GST-mPLP-E, compared with only 18% of cells in cultures treated with IL-3 alone.

Cytokines that induce hematopoietic differentiation are often capable of enhancing lineage-specific colony formation in semi-solid culture media, consistent with the results shown in FIG. 1. However, based on colony size, GST-mPLP-E alone does not appear to promote proliferation of MK progenitors and instead seems to contain only differentiation-inducing activity, similar to the activities reported for IL-6 and IL-11 (Nakashima et al., 1998, Semin. Hematol. 35:210–221), and in contrast to the combined proliferative and differentiating activities reported for TPO (Kaushansky et al., 1994, Nature 369:568–571).

Compared with control treatment of cells with both IL-3 and GST or with IL-3 alone, colonies formed in the presence of both IL-3 and GST-mPLP-E contained cells that were much larger and that exhibited more intense staining for AchE activity, as shown in FIG. 3. These characteristics are indicative of a greater degree of differentiation induced in the presence of mPLP-E than in its absence.

Figure 4:
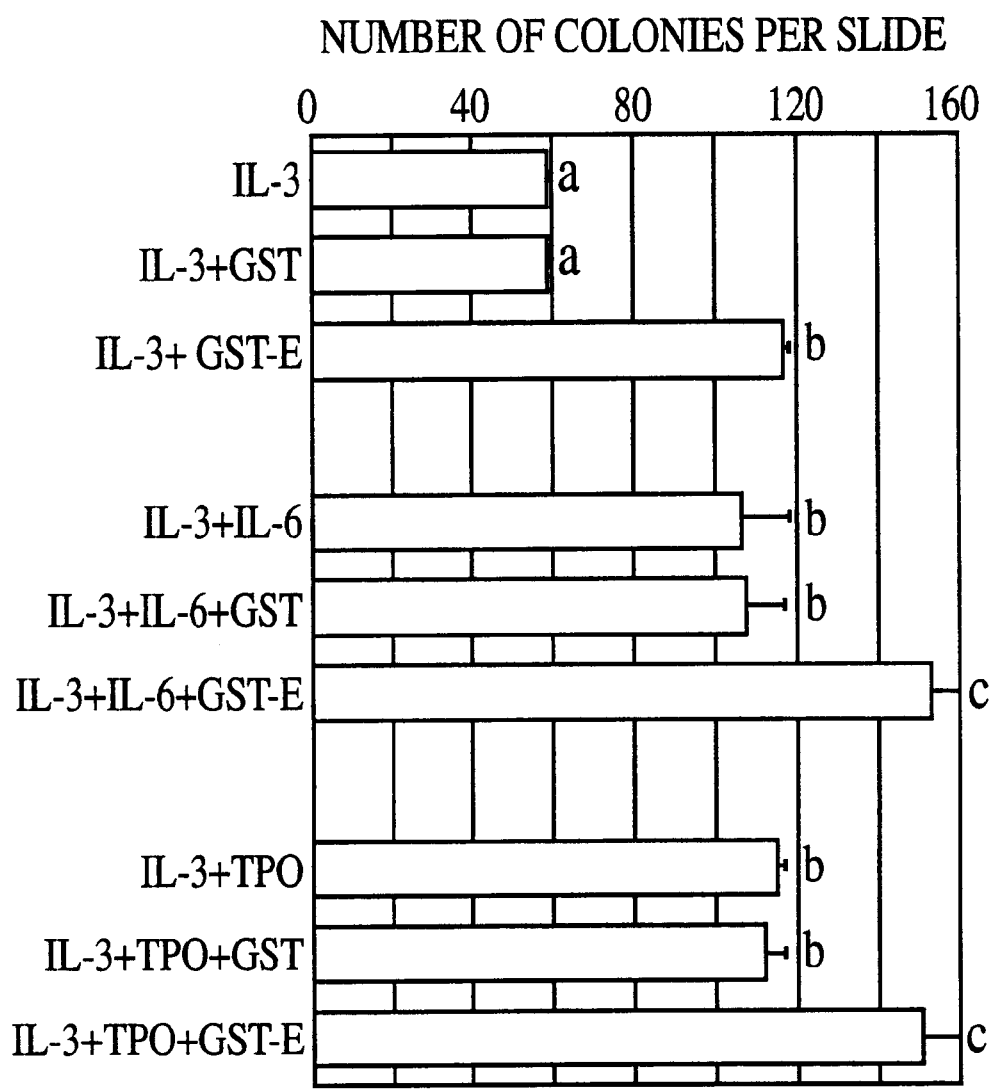
FIG. 4 is a bar graph which depicts the effects of cytokine combinations on murine CFU-MK. Results shown are obtained from duplicate assays with the observed variation, and similar results were obtained in a second independent experiment. Data were evaluated by a one-way analysis of variance followed by a Tukey's test; a versus b, p<0.01; b versus c, p<0.05; a versus c, p<0.001.

In combination with IL-3, each of GST-mPLP-E, IL-6, and TPO stimulated an approximately 2-fold increase in CFU-MK number, and in the presence of IL-6 or TPO, GST-mPLP-E treatment resulted in an additive effect on CFU-MK formation, suggesting that these factors act by means of distinct molecular targets. These results are summarized in FIG. 4. Without being bound by any particular theory of operation, these results suggest that mPLP-E directly stimulates MK progenitor proliferation, enhances progenitor cell survival, induces multipotential progenitor cells to commit to the MK lineage, or some combination thereof.

Megakaryocytopoietic Activity of mPLP-E Is Dependent on gp130

Figure 5:
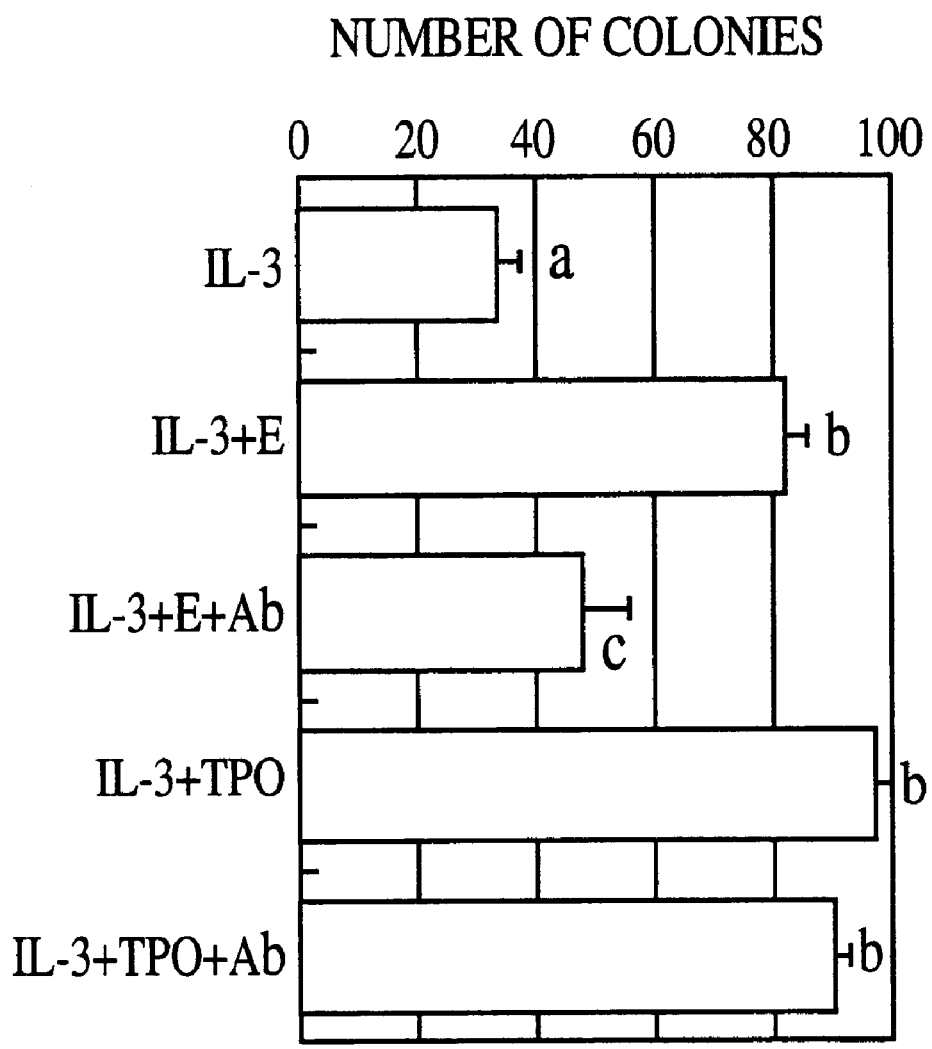
FIG. 5 is a bar graph which depicts dependence of mPLP-F activity on gp130. The number of murine MK colonies obtained under conditions described herein was scored, with the combination of results from two experiments shown; a versus b, p<0.001; b versus c, p<0.01. Similar results were obtained in another independent experiment. "Ab" refers to the antibody added to the assay mixture to interfere with gp130-dependent signaling.

Several cytokines that induce MK cell differentiation act by means of heteromeric receptor complexes that include the signal transducing transmembrane protein, gp130. To test the hypothesis that mPLP-E also signals by means of gp130, monoclonal antibodies that block gp130 signaling were added along with GST-mPLP-E to primary bone marrow cultures. These antibodies completely abolished MK differentiation in response to GST-mPLP-E. Colonies grown in the presence of GST-mPLP-E and these antibodies contained MK cells of a small size similar to cultures treated with IL-3 alone. In contrast, TPO-induced MK differentiation was not affected by addition of these antibodies, consistent with TPO signaling through a distinct pathway. Furthermore, blockade of gp130 signaling significantly reduced GST-mPLP-E-induced colony formation, whereas gp130 antibodies had no detectable effect on TPO activity in this assay, as indicated by the results summarized in FIG. 5.

The effective dose of mPLP-E in the induction of MK cell differentiation is high relative to effective concentrations for many other cytokines. However, this is a common finding for placental hormones, which are typically produced in massive amounts, and the several-microgram per milliliter range is physiologically relevant for mPLP-E. This activity cannot be attributed to a contaminant in the preparation, because comparable preparations of GST alone or of a related GST/prolactin-like fusion protein, GST-mPLP-B, have no activity in these assays, because AP-mPLP-E protein demonstrates specific binding of mPLP-E with MK cells, and because the cytokine activity is recovered from bacterial cells (i.e., which do not produce any other mammalian factors).

Another murine placental-specific hormone, designated mPLP-F, is very similar in sequence to mPLP-E. The amino acid sequence of each of these two proteins has been described, as has the nucleotide sequence encoding each (Lin et al., 1997, Endocrinology 138:5535–5540). mPLP-F also binds specifically with MK cells, and can exhibit the same activities described herein for mPLP-E.

Analysis of the amino acid sequence of MPLP-E indicates that the hormone is likely glycosylated. Molecular forms of mPLP-E that are larger than would be expected from the primary amino acid sequence alone are detected in maternal murine plasma. Glycosylation can contribute to the half-life of mPLP-E in the maternal circulation, to the distribution of this hormone (for example, glycosylation may determine whether or not mPLP-E can enter the fetal compartment), or to maximal affinity for receptor. However, glycosylation of mPLP-E is not necessary in order for it to exhibit for receptor binding or the other activities described herein.

Without being bound by any particular theory of operation, the inventors believe that the fact that antibodies which bind specifically with gp130 block mPLP-E induction of MK cell differentiation is an indication that mPLP-E function probably involves interaction of mPLP-E with a cell surface-binding protein, followed by an interaction of the mPLP-E-binding protein pair with gp130. The binding subunit may only recognize mPLP-E, but this seems unlikely because mPLP-E was also found to bind with adult male and adult, non-pregnant female MK cells. These cells would not normally be exposed to a placenta-specific hormone.

Several cytokines, including IL-6, IL-11, leukemia inhibitory factor, and ciliary neurotrophic factor, are megakaryocytopoietic and participate in signaling involving gp130. This observation is consistent with gp130 providing an important regulatory target for MK development and platelet production. mPLP-E is therefore a useful probe for identifying additional cytokine receptors on MK cells that may be therapeutically targeted for the clinical regulation of platelet production.

EXAMPLE 2 mPLP-E Acts as a Multi-lineage Survival Factor for Human Hematopoietic Progenitor Cells In the experiments presented in this example, the effects of mPLP-E on expansion of purified $CD34^+$ human bone marrow cells in culture are described.

The materials and methods used in the experiments presented in this example are now described.

Preparation of Low-density Non-adherent Mononuclear Cells from Peripheral Blood Aphereses Bone marrow were obtained from femurs of individual hematologically normal human patients who were undergoing total hip arthroplasty. The bone marrow samples were collected in an anti-coagulant preparation in order to prevent platelet activation. This anti-coagulant preparation comprised 50 units per milliliter preservative-free heparin (Life Technologies, Gaithersburg, Md.), 1 millimolar Na-EDTA, 1 millimolar adenosine, 2 millimolar theophylline, 2.2 micromolar prostaglandin $E_1$ (Sigma Co., St. louis, Mo.), and 0.1 milligram per milliliter DNase I (Boehringer Mannheim, Indianapolis, Ind.) in 20 milliliters Iscove's Modified Dulbecco's Medium, (IMDM, Life Technologies). Marrow cells were repeatedly extracted from bone fragments using IMDM comprising 0.1 milligram per milliliter DNase I (Boehringer Mannheim) and 4 micrograms per milliliter gentamicin (Life Technologies).

Bone marrow extract was homogenized by passing it through an 18 gauge needle in order to remove bone fragments. Residual red cells were lysed using ORTHO-MUNE™ lysing reagent (Ortho Diagnostics), and the remaining cells were recovered by centrifugation for 6 minutes at 420×g through a 10% (w/v) human serum albumin cushion.

Purification of CD34+ Cells

CD34+ cells (i.e., cells expressing the CD34 marker) were purified using magnetic cell sorting using a MINIMACS™ cell sorting system (Miltenyi Biotec, Auburn, Calif.) following the manufacturer's recommendations and otherwise as described by Miltenyi et al. (1990, Cytometry 11:231–238). Cells were passed over two columns and eluted with X-VIVO™ 20 reagent (BioWhittaker). 93.4%±1.0% of cells were viable, as assessed using a standard Trypan Blue exclusion assay, and the average purity was 90.9%±1.7% CD34+ cells, as assessed by flow cytometry.

Culture Conditions

For each selected cytokine combination, about $4 \times 10^5$ Trypan Blue-negative cells were cultured per milliliter of serum-free nutritive medium. Cultures were maintained for 13 days at 37° C. in a fully humidified 5% (v/v) $CO_2$ atmosphere. Thrombopoietin (TPO), stem cell factor (SCF), and flt-3 ligand (Flt-3L; all obtained from R&D Systems, Minneapolis, Minn.) were each added to selected media to a final concentration of 100 nanograms per milliliter. mPLP-E was used at a concentration of 4 micrograms per milliliter. Cell numbers in the cultures were assessed in the presence of Trypan Blue at days 0, 3, 6, 9, and 13 following the beginning of ex vivo maintenance. If the cell number exceeded $8 \times 10^5$ in any culture, then the cell number was re-adjusted to about $4 \times 10^5$ by diluting the culture with fresh medium containing the same cytokines. Only Trypan Blue-negative cells were counted and used for calculating cell proliferation and MK production.

Clonogenic Assay

Clonogenic assays were performed using a serum-free collagen medium (MEGACULT-C™, Stem Cell Technologies, Vancouver, BC) for CFU-MK determinations, and using a methylcellulose culture medium (METHOCULT GF+™, Stem Cell Technologies) for CFU-GM, CFU-GEMM, and BFU-E determinations. All assays were performed according to the medium manufacturer's instructions. An aliquot containing about 1,000 cells from each sample was mixed with the assay medium and plated. CFU-MK were scored after ten days, and CFU-GM, CFU-GEMM, and BFU-E were scored after fourteen days. CFU-MK maturity was evaluated by counting the number of cells in each colony. Three size categories were defined—one including (small mature) colonies of 3–20 cells, a second including (medium-sized) colonies of 21–50 cells, and a third including (large immature) colonies of >50 cells.

Flow Cytometric Analysis

Cell aliquots were washed in phosphate-buffered saline (PBS, GIBCO) comprising 5 millimolar EDTA and 1% (w/v) bovine serum albumin (Sigma). This washing solution was used to prevent further platelet activation and reverse adherence of activated platelets, as described (Dercksen et al., 1995, Blood 86:3771–3782). After washing, the cells were stained for 15 minutes at 4° C. in the dark with phycoerythrin-cyanin 5.1-(PC5-)conjugated anti-CD34 antibody (Clone 581, Coulter-Immunotech, Miami, Fla.), phycoerythrin-(PE-)conjugated anti-CD41 antibody (Coulter-Immunotech), and fluorescein isothiocyanate-(FITC-)conjugated anti-CD15 (Coulter-Immunotech.

Stained cells were analyzed by flow cytometry. Negative controls that were used included PC5-, PE-, and FITC-conjugated anti-mouse $IgG_1$ antibodies used at equivalent $IgG_1$ concentrations. Only the non-apoptotic high forward scatter, low side scatter, cell population was used for subset analysis.

DNA degradation products (i.e., <2N DNA, reflecting apoptosis) and megakaryocyte ploidy content were also measured by flow cytometry. FITC-conjugated anti-CD41 antibody-stained cells were washed again in 1% BSA-PBS and re-suspended in a solution comprising 1 milligram per milliliter sodium citrate with 50 micrograms per milliliter 7-aminoactinomycin D (Sigma). Re-suspended cells were incubated for 30 minutes or more at 4°–8° C. in the dark, as described (Jackson et al., 1984, Blood 63:768–778). All samples were analyzed on the same day using a 3-color laser.

The results of the experiments presented in this example are now described.

Specific Binding of mPLP-E with Human MK Cells

In order to determine if specific mPLP-E binding sites are present on human MKs, CD34+ bone marrow hematopoietic progenitor cells were maintained in nutritive medium in the presence of TPO, SCF, and Flt3 ligand (Flt3-L). The cells were subsequently incubated with AP-mPLP-E fusion protein, and binding of the fusion protein with cells was assessed. Binding of the fusion protein could be detected both with large, differentiated MK cells and with small cells. The binding could be completely eliminated in the presence of excess GST-mPLP-E fusion protein, but not in the presence of GST. These results indicate that mPLP-E binds specifically with a cell surface receptor present on human MK cells.

Effect of mPLP-E on Total and Progenitor Cell Expansion

Figure 6:
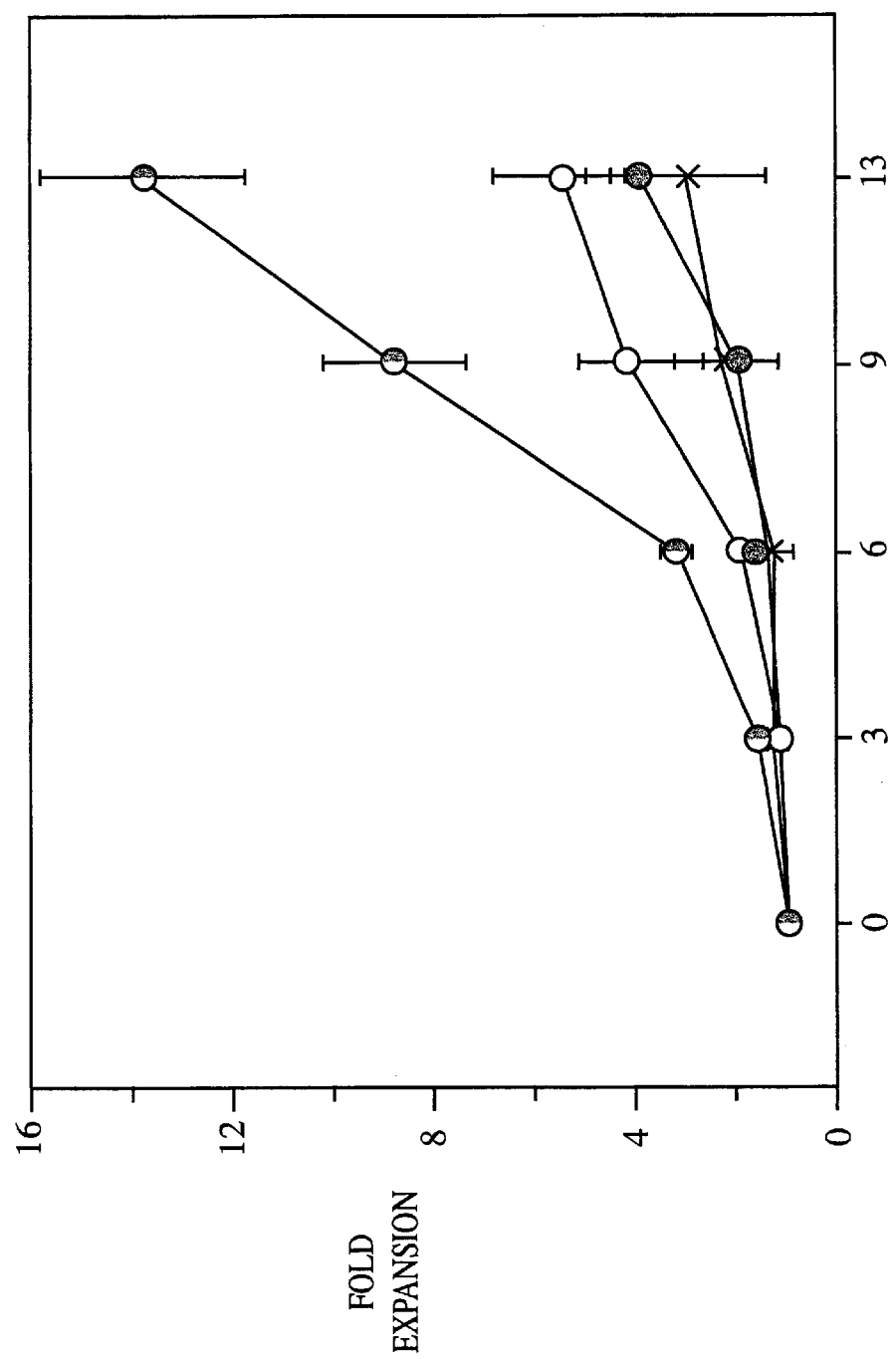
FIG. 6 is a graph which depicts the results of experiments described herein for determining the extent of expansion of viable cells derived from CD34$^+$ cells purified from human bone marrow when the cells were maintained ex vivo in nutritive medium comprising mPLP-E ("PLP"), TPO, both, or neither (i.e., "GST").
Figure 7A:
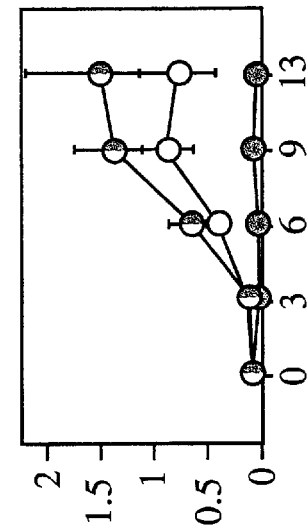
FIGS. 7A–7D, is a quartet of graphs which depict the results of experiments in which viable cells derived from CD34$^+$ cells purified from human bone marrow were maintained ex vivo in nutritive medium comprising mPLP-E (filled circles), TPO (open circles), both (half-filled circles), or neither (crosses).
Figure 7B:
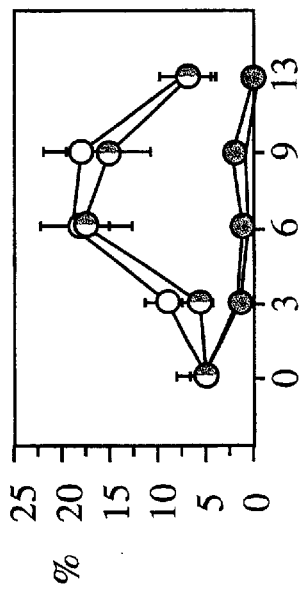
Figure 7C:
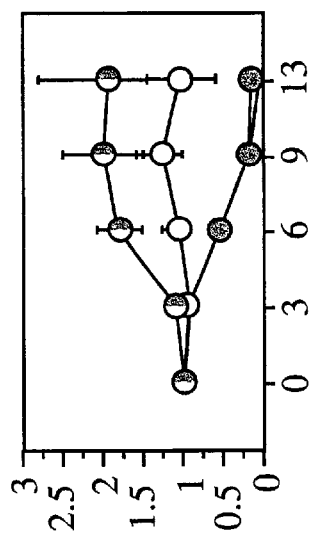
Figure 7D:
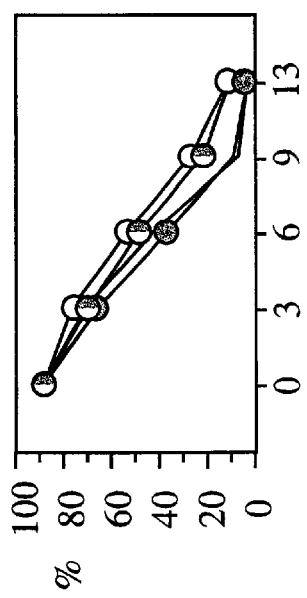
Figure 9E:
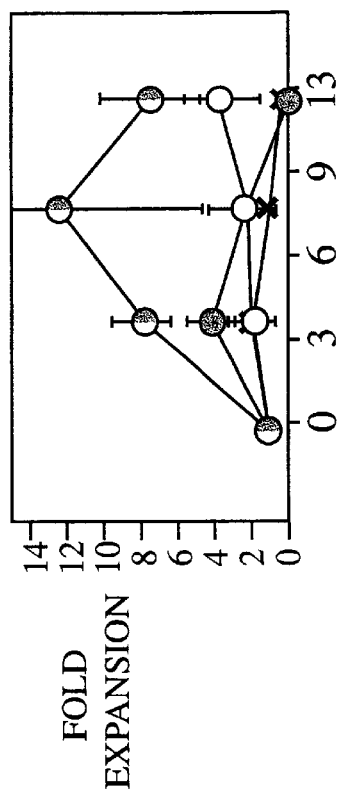
Figure 9F:
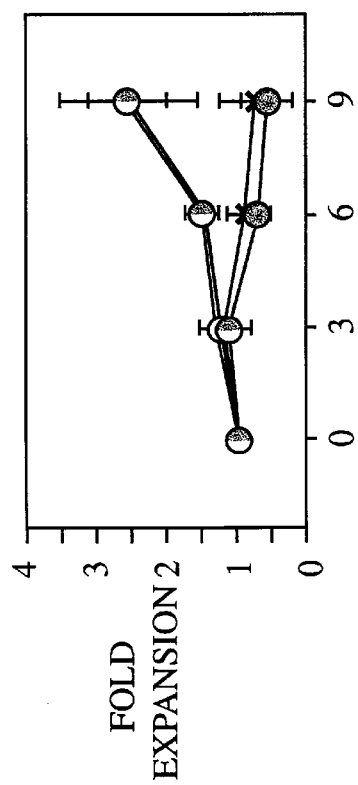
Figure 9G:
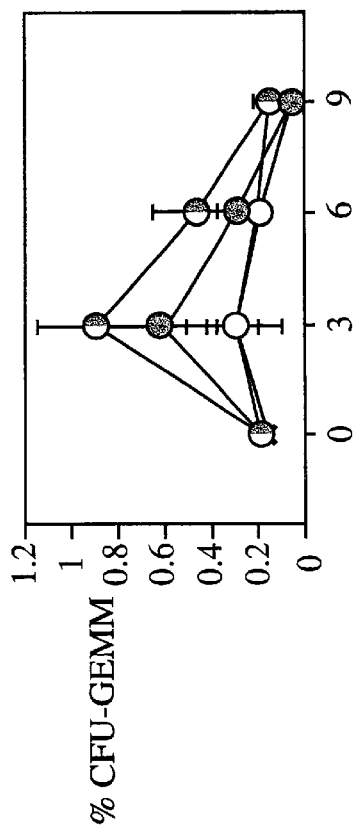
Figure 9H:
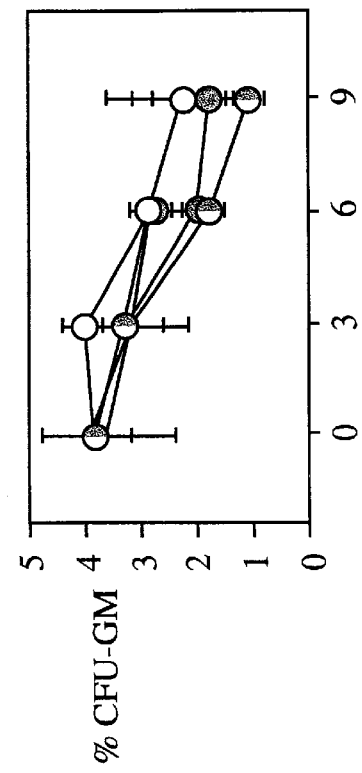

CD34+ cell samples obtained from 6 humans were seeded in serum-free nutritive medium that comprised one or both of mPLP-E and thrombopoietin (TPO). Total cell number increased under all conditions tested. Starting at day 6 following ex vivo culture, the combined effects of mPLP-E and TPO in the medium were synergistic and significantly increased total cell expansion relative to medium comprising only one of mPLP-E and TPO. Neither medium comprising TPO (but not mPLP-E) nor medium comprising mPLP-E (but not TPO) resulted in an increase in total cell expansion significantly greater than was achieved using medium comprising GST (but neither TPO nor mPLP-E; i.e., a control medium). The results of these experiments are presented in FIG. 6.

The frequency of CD34+/CD41+ cells increased significantly after 3, 6 and 9 days of maintenance in nutritive medium comprising both mPLP-E and TPO, relative to the frequency of these cells at day 0, as indicated by the results presented in FIG. 7. The increased frequency of CD34+/CD41+ cells achieved using mPLP-E and TPO was greater than the increase achieved using medium which comprised mPLP-E (but not TPO), medium which comprised TPO (but not mPLP-E), and medium which comprised neither TPO nor mPLP-E.

Effect of PLP-E on Megakaryocyte Production

Starting at day 6, CD34+ cell cultures maintained in nutritive medium comprising both mPLP-E and TPO comprised significantly more CD41+ cells per seeded CD34+ cell than cultures maintained in medium which contained TPO but not mPLP-E. The increase in megakaryocyte expansion was primarily due to increased cell proliferation, since mPLP-E alone did not promote human CD41 marker expression, and, until day 13, significantly decreased TPO-induced CD41+ frequency when used together with TPO in medium. The results of these experiments are presented in FIG. 8.

Cultured cells were assayed at selected intervals in order to determine CFU-MK, CFU-GM (colony-forming units-granulomacrocytic cells), CFU-GEMM (colony-forming units-multi-lineage-potential hematopoietic progenitor cells), and BFU-E (burst-forming units-erythrocytes) expansion. Nutritive medium comprising both mPLP-E and TPO induced significant expansion of all colony lineages measured at all time points, as indicated by the results presented in FIG. 9. Compared to medium comprising TPO (but not mPLP-E), medium comprising both PLP-E and TPO significantly increased expansion of CFU-MK, BFU-E, and CFU-GEMM at each day measured, but had no significant effect on CFU-GM expansion. PLP-E alone significantly increased the number of CFU-GEMM obtained after 3 days in culture. PLP-E alone had no significant positive effect of on BFU-E, CFU-GM, or CFU-MK expansion.

CFU-MK Maturation

Figure 10:
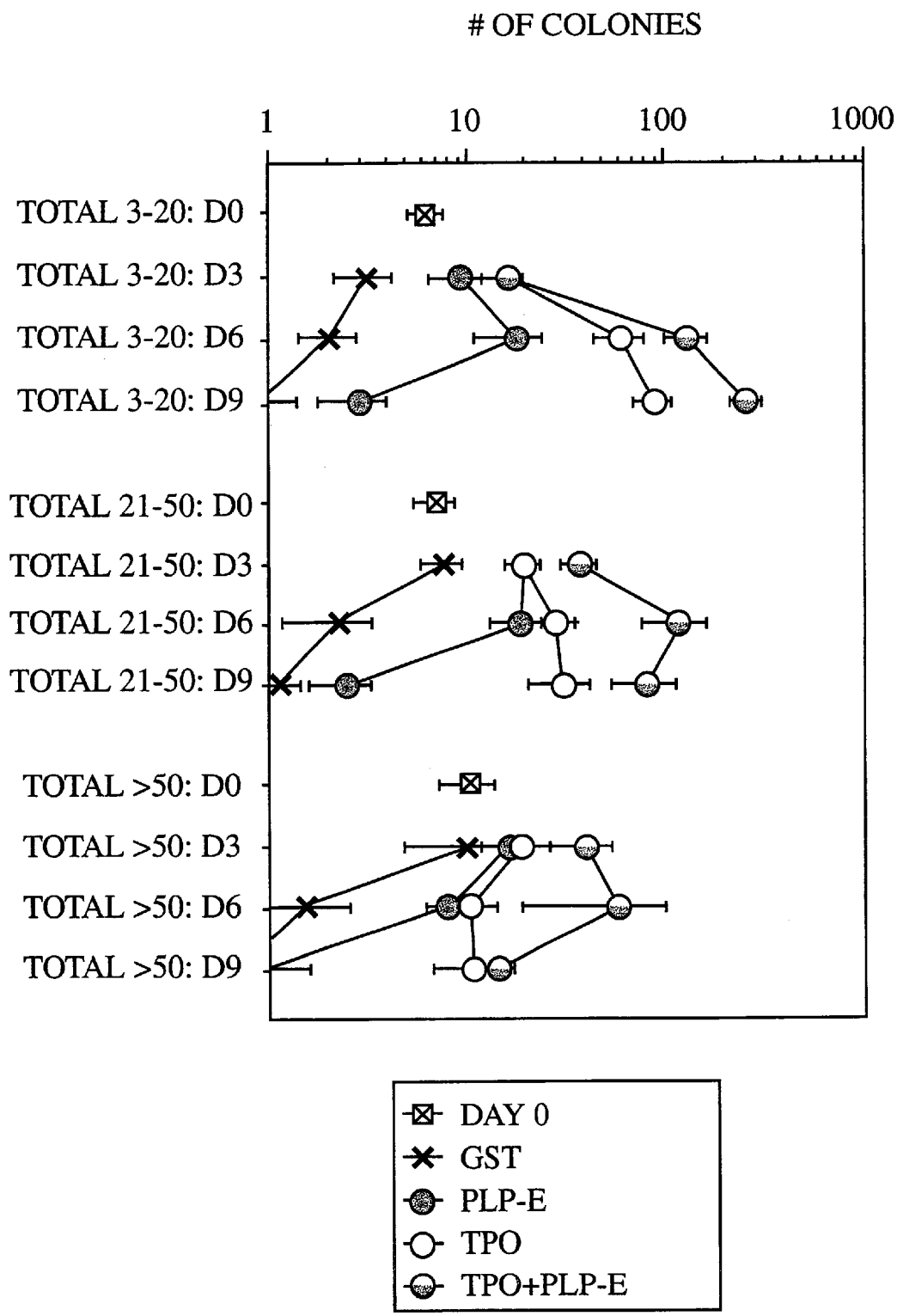
FIG. 10 is a graph which depicts CFU-MK expansion in cells derived from CD34$^+$ cells purified from human bone marrow in cell cultures maintained in the presence of medium comprising mPLP-F (filled circles), TPO (open circles), both (half-filled circles), or neither (crosses). The data are presented as the number of colonies in each of the indicated CFU-MK maturation subsets (i.e., 3–20 cells per colony; 21–50 cells per colony; and >50 cells per colony) per 1000 CD34$^+$ cells assayed.

The number of cells in each CFU-MK colony is an indication of the maturity of the progenitor population. For example, large colonies generally derive from less mature progenitor cells. CD34+ cells comprising 2.4%±0.4% CFU-MK were used to seed nutritive medium comprising mPLP-E, TPO, both, or neither, and the media were maintained for 9 days. When colonies of the CD34+ CFU-MK used to seed the media were assessed for relative maturity by size, 40.4%±5.6% of the colonies were derived from primitive CFU-MK, containing more than 50 cells. Intermediate (21–50 cells per colony) and mature (<20 cells per colony) CFU-MK represented 28.9%±2.6% and 30.7%±7.7% of the seeded CFU-MK, respectively. The seeded media were incubated and sampled at days 0, 3, 6, and 9 of incubation, and the sub-fraction of CFU-MK colonies assignable to each of these three subsets was assessed in the samples. The results of these experiments are depicted in FIG. 10.

The fraction of CFU-MK in each of the three subsets was greater at 3 days incubation than at day 0 in cultures which contained mPLP-E (but which did not contain TPO). The fraction of CFU-MK in the mature and intermediate subsets was also greater in these cultures at day 6 of incubation than at day 0. CFU-MK maintained in medium comprising TPO (but not comprising mPLP-E) exhibited similar expansion. When the cells were maintained in medium that comprised both mPLP-E and TPO, all three subsets expanded to a significantly greater degree than they did when the cells were maintained in medium comprising TPO (but not mPLP-E). Cells maintained in medium comprising both mPLP-E and TPO exhibited significant expansion of the primitive subset of CFU-MK at both day 6 and 9. GST-treated control samples could not maintain any significant number of CFU-MK.

Without being bound by any particular theory of operation, the inventors believe that mPLP-E acts as an early survival factor for primitive human progenitor cells of the megakaryocytic and erythroid lineages. mPLP-E preserves the highly proliferative nature of the immature fraction of the hematopoietic progenitor cells, but does not by itself promote human MK production or increase total cell proliferation. Thus, mPLP-E can be used in combination with TPO and/or other cytokines for ex vivo expansion of hematopoietic progenitor cells, mPLP-E serving to maintain a pool of immature progenitor cells having a high proliferative capacity, and TPO or other cytokines serving to stimulate at least a fraction of those immature cells to differentiate into cells of a desired lineage or type.

The disclosure of every patent, patent application, and publication cited herein is hereby incorporated herein by reference in its entirety.

While this invention has been disclosed with reference to specific embodiments, it is apparent that other embodiments and variations of this invention can be devised by others skilled in the art without departing from the true spirit and scope of the invention. The appended claims include all such embodiments and equivalent variations.

What is claimed is:

1. A method of maintaining mammalian hematopoietic progenitor cells in vitro, the method comprising maintaining the cells in vitro in a nutritive medium comprising murine prolactin-like protein E (mPLP-E).

2. The method of claim 1, wherein the mPLP-E has the amino acid sequence SEQ ID NO: 2.

3. The method of claim 2, wherein the mPLP-E is glycosylated at at least one of residues 6, 28, 80, 119, 127, and 234 of SEQ ID NO: 2.

4. The method of claim 1, wherein the nutritive medium further comprises a cytokine selected from the group consisting of thrombopoietin, interleukin-3, interleukin-6, interleukin-11, leukemia inhibitory factor, and kit ligand.

5. The method of claim 1, wherein the nutritive medium further comprises a cytokine selected from the group consisting of thrombopoietin, interleukin-3, stem cell factor, and flt3 ligand.

6. The method of claim 1, wherein the nutritive medium further comprises thrombopoietin.

7. The method of claim 6, wherein the nutritive medium further comprises stem cell factor and flt3 ligand.

8. The method of claim 1, wherein the nutritive medium further comprises interleukin-3.

9. The method of claim 1, wherein the cells are human hematopoietic progenitor cells.

10. The method of claim 1, wherein the cells are obtained from bone marrow of a mammal.

11. The method of claim 1, wherein the cells are obtained from a fetal mammal.

12. The method of claim 1, wherein the cells are obtained from cord blood.

13. The method of claim 1, wherein the cells are maintained in the nutritive medium for at least about 3 days.

14. A method of inducing proliferation of mammalian hematopoietic progenitor cells in vitro, the method comprising maintaining the cells in vitro in a nutritive medium comprising mPLP-E.

15. A method of expanding mammalian hematopoietic progenitor cells in vitro, the method comprising maintaining the cells in vitro in a nutritive medium comprising mPLP-E.

16. A method of inducing differentiation of mammalian hematopoietic progenitor cells in vitro, the method comprising maintaining the cells in vitro in a nutritive medium comprising mPLP-E.

17. A method of inducing mammalian hematopoietic progenitor cells to differentiate in vitro into megakaryocytes, the method comprising maintaining the cells in vitro in a nutritive medium comprising mPLP-E.

18. A method of inducing mammalian megakaryocytes to differentiate into platelets, the method comprising contacting the megakaryocytes with mPLP-E.

19. The method of claim 18, wherein the megakaryocytes are contacted with mPLP-E in vitro.

20. In an in vitro method of maintaining mammalian hematopoietic progenitor cells, the improvement comprising maintaining the cells in the presence of mPLP-E.

* * * * *